(12) United States Patent
Rademacher et al.

(10) Patent No.: US 6,716,592 B1
(45) Date of Patent: Apr. 6, 2004

(54) MATERIALS AND METHODS RELATING TO THE DIAGNOSIS AND TREATMENT OF DIABETES AND OBESITY

(75) Inventors: Thomas William Rademacher, Oxford (GB); Patricia McLean, Surrey (GB)

(73) Assignee: Rodaris Pharmaceuticals Limited, Oxford (GB)

( * ) Notice: Subject to any disclaimer, the term of this patent is extended or adjusted under 35 U.S.C. 154(b) by 0 days.

(21) Appl. No.: 09/254,800

(22) PCT Filed: Sep. 11, 1997

(86) PCT No.: PCT/GB97/02440

§ 371 (c)(1),
(2), (4) Date: Jun. 11, 1999

(87) PCT Pub. No.: WO98/11435

PCT Pub. Date: Mar. 19, 1998

(30) Foreign Application Priority Data

Sep. 11, 1996 (GB) ............................................. 9618934

(51) Int. Cl.[7] ............................................ G01N 33/573

(52) U.S. Cl. ......................................... 435/7.4; 435/4

(58) Field of Search ...................................... 435/4, 7.4

(56) References Cited

U.S. PATENT DOCUMENTS

| | | | |
|---|---|---|---|
| 5,122,603 A | 6/1992 | Larner et al. | 536/18.7 |
| 5,183,764 A | 2/1993 | Kennington et al. | 436/131 |
| 5,427,956 A | 6/1995 | Kennington et al. | 436/131 |
| 5,750,348 A | 5/1998 | Larner | 435/7.1 |

FOREIGN PATENT DOCUMENTS

| | | |
|---|---|---|
| EP | 0 532 915 A3 | 3/1993 |
| WO | WO 96/29425 | 9/1996 |

OTHER PUBLICATIONS

The Merck Manual of Diagnosis and Therapy. 17th Edition, Merck Research Laboratories, 1999, pp. 165–171.*

Alberti K.G.M.M. and Press, C.M. "The Biochemistry of the Complications of Diabetes Mellitus," *Complications of Diabetes* Eds Keen, H. and Jarret, J. Publishers Edward Arnold Ltd., London, pp. 231–270 (1982).

Asplin, I. et al., "chiro–inositol Deficiency and Insulin Resistance: A Comparison of the chiro–Inositol–and the myo–Inositol–Containing Insulin Mediators Isolated from Urine, Hemodialysate, and Muscle of Control and Type II Diabetic Subjects," 90 *Proc. Natl. Acad. Sci.* 5924–5928 (1993).

Baron, A., "The Coupling of Glucose Metabolism and Perfusion in Human Skeletal Muscle. The Potential Role of Endothelium–Derived Nitric Oxide," 45 (Suppl. 1) *Diabetes* S105–S109 (1996).

Bennett, P. et al., "Epidemiology and Natural History of NIDDM: Non–obese and Obese," In: *International Textbook of Diabetes Mellitus*, Eds. Alberti, K. et al. John Wiley & Sons Ltd., pp. 147–169 (1992).

Brautigan, D., "Protein Phosphatases," 49 *Recent Prog. Hormone Res.* 197–214 (1994).

Caro, H.N. et al., "Isolation and partial characterisation of insulin–mimetic inositol phosphoglycans from human liver," 61 *Biochemical and Molecular Medicine* 214–228 (Aug. 1997).

Cohen, P., "The Structure and Regulation of Protein Phosphatases," 58 *Annu. Rev. Biochem.* 453–508 (1989).

Craig, J. et al., "Chiroinositol Deficiency and Insulin Resistance," In: *Molecular Biology of Diabetes. Part II*, Eds. Draznin, B. and LeRoith, D., Humana Press Inc., Totowa, NJ, pp. 343–362 (1994).

DeFronzo, R. et al., "Efficacy of Metformin in Patients with Non–Insulin–Dependent Diabetes Mellitus," 333(9) *The New England Journal of Medicine* 541–549 (1995).

DeFronzo, R. et al., "Pathogenesis of NIDDM: A Balanced Overview," 15(3) *Diabetes Care* 318–368 (1992).

DeFronzo, R., "The Triumvirate: β–Cell, Muscle, Liver: A Collusion Responsible for NIDDM," 37 *Diabetes* 667–687 (1988).

Farese, R. et al., "Insulin–Induced Activation of Glycerol–3–Phosphate Acyltransferase by chiro–Inositol–Containing Insulin Mediator is Defective in Adipocytes of Insulin Resistant, Type II Diabetic Goto–Kakizaki Rats," 91 *Proc. Natl. Acad. Sci.* 11040–11044 (1994).

Ferrannini, E., "Physiological and Metabolic Consequences of Obesity," 44(9) (Suppl. 3) *Metabolism* 15–17 (1995).

Fonteles, M.C. et al., "Infusion of pH 2.0 D–chiro inositol glycan insulin putative mediator normalizes plasma glucose in streptozotocin diabetic rats at a dose equivalent to insulin without inducing hypoglycaemia," *Diabetologia* 39:731–734 (1996).

Himsworth, H., "Diabetes Mellitus: Its Differentiation Into Insulin–Sensitive and Insulin–Insensitive Types," *The Lancet* 127–130 (1936).

Huang, L. et al., "Chiroinositol Deficiency and Insulin Resistance. III. Acute Glycogenic and Hypoglycemic Effects of Two Inositol Phosphoglycan Insulin Mediators in Normal and Streptozotocin–Diabetic Rats in Vivo," 132(2) *Endocrinology* 652–657 (1993).

Kennington, A. et al., "Low Urinary chiro–Inositol Excretion in Non–Insulin Dependent Diabetes Mellitus," 323(6) *The New England Journal of Medicine* 373–378 (1990).

(List continued on next page.)

Primary Examiner—Patrick J. Nolan
(74) Attorney, Agent, or Firm—Emily M. Haliday; Quine Intellectual Property Law Group, P.C.

(57) ABSTRACT

The diagnosis of diabetes based on the level or ratio of P- and A-type inositolphosphoglycans (IPGs) in a sample from a patient is disclosed.

29 Claims, 7 Drawing Sheets

OTHER PUBLICATIONS

Krentz, A. and Nattrass, M., "Insulin Resistance: A Multifaceted Metabolic Syndrome. Insights Gained Using a Low-Dose Insulin Infusion Technique," 13 *Diabetic Medicine* 30–39 (1996).

Kubota, M. et al., "Portal Insulin Delivery is Superior to Peripheral Delivery in Handling of Portally Delivered Glucose," 45(2) *Metabolism* 150–154 (1996).

Kunjara, S. et al., "Tissue Specific Release of Inositol Phosphogylcans," In: *Biopolymers and Bioproducts: Structure, Function, and Applications*, J. Svast et al. (ed), Dokya Publications, pp. 301–306 (1995).

Larner, J. et al., "Insulin Mediators and the Control of Pyruvate Dehydrogenase Complex," 573 *Annals New York Academy of Sciences* 297–305 (1989).

Larner, J. et al., "Insulin Mediators: Structure and Formation," 53 *Cold Spring Harbour Symposia on Quantitative Biology* 965–971 (1988).

Lazar, D. et al., "Stimulation of Glycogen Synthesis by Insulin in Human Erythroleukemia Cells Requires the Synthesis of Glycosyl–Phosphatidylinositol," 91 *Proc. Natl. Acad. Sci.* 9665–9669 (1994).

Lilley, K. et al., "Insulin Mediator Stimulation of Pyruvate Dehydrogenase Phosphatases," 296(1) *Archives of Biochemistry and Biophysics* 170–174 (1992).

Machicao, F. et al., "Mannose, Glucosamine and Inositol Monophosphate Inhibit the Effects of Insulin on Lipogenesis. Further Evidence for a Role for Inositol Oligosaccharides in Insulin Action," 266 *Biochem. J.* 909–916 (1990).

Martiny, L. et al., "Control by Thyotropin of the Production by Thyroid Cells of an Inositol Phosphate–Glycan," 2(1) *Cell Signalling* 21–27 (1990).

Misek, D. and Saltiel, A., "An Inositol Phosphate Glycan Derived From a *Trypanosoma brucei* Glycosyl Phosphatidylinositol Promotes Protein Dephosphorylation in Rat Epididymal Adipocytes," 135(5) *Endocrinology* 1869–1876 (1994).

Moller, D. and Flier, J.S., "Insulin Resistance—Mechanisms, Syndromes, and Implications," 325(13) *The New England Journal of Medicine* 938–948 (1991).

Moncada, S. and Higgs, A., "The L–Arginine–Nitric Oxide Pathway," 329(27) *The New England Journal of Medicine* 2002–2012 (1993).

Muller, G. et al., "The Sulphonylurea Drug, Glimepiride, Stimulates Release of Glycosylphosphatidylinositol–Anchored Plasma–Membrane Proteins from 3T3 Adipocytes," 289 *Biochem. J.* 509–521 (1993).

Newman, J. et al., "Assay of Insulin Mediator Activity with Soluble Pyruvate Dehydrogenase Phosphatase," 116(5) *Endocrinology* 1912–1919 (1985).

O'Rahilly, S. and Moller, D., "Mutant Insulin Receptors in Syndromes of Insulin Resistance," 36 *Clinical Endocrinology* 121–132 (1992).

Ortmeyer, H. et al., "Chiroinositol Deficiency and Insulin Resistance. I. Urinary Excretion Rate of Chiroinositol is Directly Associated with Insulin Resistance in Spontaneously Diabetic Rhesus Monkeys," 132(2) *Endocrinology* 640–645 (1993).

Ortmeyer, H. et al., "Chiroinositol Deficiency and Insulin Resistance. II. Acute Effects of D–Chiroinositol Administration in Streptozotocin–Diabetic Rats, Normal Rats Given a Glucose Load, and Spontaneously Insulin–Resistant Rhesus Monkeys," 132(2) *Endocrinology* 646–651 (1993).

Ortmeyer, H. et al., "In vivo D–chiroinositol activates skeletal muscle glycogen synthase and inactivates glycogen phosphorylase in rhesus monkeys," 6 *Journal of Nutritional Biochemistry* 499–503 (1995).

Ostlund, R. et al., "D–chiro–Inositol Metabolism in Diabetes Mellitus," 90 *Proc. Natl. Acad. Sci.* 9988–9992 (1993).

Panzram, G., "Mortality and Survival in Type 2 (Non–Insulin–Dependent) Diabetes Mellitus," 30 *Diabetologia* 123–131 (1987).

Polonsky, K. et al., "Non–Insulin–Dependent Diabetes Mellitus—A Genetically Programmed Failure of the Beta Cell to Compensate for Insulin Resistance," 334(12) *Seminars in Medicine of the Beth Israel Hospital, Boston* 777–783 (1996).

Prochazka, M. et al., "Molecular and Linkage Analysis of Type–1 Protein Phosphatase Catalytic Beta–Subunit Gene: Lack of Evidence for its Major Role in Insulin Resistance in Pima Indians," 38 *Diabetologia* 461–466 (1995).

Rademacher, T. et al., "Inositolphosphoglycan Second Messengers," 27 *Brazilian J. Med. Biol.* 327–341 (1994).

Reaven, G. et al., "Hypertension and Associated Metabolic Abnormalities—The Role of Insulin Resistance and the Sympathoadrenal System," 334(6) *The New England Journal of Medicine* 374–381 (1996).

Reaven, G., "Banting Lecture 1998. Role of Insulin Resistance in Human Disease," 37 *Diabetes* 1595–1607 (1988).

Reaven, G., "Pathophysiology of Insulin Resistance in Human Disease," 75(3) *Physiological Reviews* 473–486 (1995).

Rodbell, M., "Metabolism of Isolated Fat Cells," 239(2) *The Journal of Biological Chemistry* 375–380 (1964).

Romero, G. and Larner, J., "Insulin Mediators and the Mechanism of Insulin Action," 24 *Advances in Pharmacology* 21–50 (1993).

Romero, G. et al., "Anti–Inositolglycan Antibodies Selectivity Block Some of the Actions of Insulin in Intact $BC_3H1$ Cells," 87 *Proc. Natl. Acad. Sci.* 1476–1480 (1990).

Romero, G. et al., "Phosphatidylinositol–Glycan Anchors of Membrane Proteins: Potential Precursors of Insulin Mediators," 240 *Science* 509–511 (1988).

Romero, G., "Inositolglycans and Cellular Signaling," 15 *Cell Biology International Reports* 827–852 (1991).

Saltiel, A. et al., "The Role of Glycosylphosphoinositides in Signal Transduction," 45 *Recent Prog. Horm. Res.* 353–382 (1989).

Sanchez–Arias, J. et al., "Impairment of Glycosyl–Phosphatidylinositol–Dependent Insulin Signaling System in Isolated Rat Hepatocytes by Streptozotocin–Induced Diabetes," 131(4) *Endocrinology* 1727–1733 (1992).

Serrano, J. et al., "Insulin Resistance: Cellular and Molecular Mechanisms," In: *Recent Advances in Endocrinology and Metabolism*, vol. 4, pp. 167–183 (1992).

Sochor, M. et al., "Glucose Over– and Underutilization in Diabetes: Comparative Studies of the Change in Activities of Enzymes of Glucose Metabolism in Rat Kidney and Liver," 7 *Molecular Physiology* 51–67 (1985).

Stumvoll, M. et al., "Metabolic Effects of Metformin in Non–Insulin–Dependent Diabetes Mellitus," 333(9) *The New England Journal of Medicine* 550–554 (1995).

Suzuki, S et al., "Molecular Mechanism of Insulin Resistance in Spontaneous Diabetic GK (Goto–Kakizaki) Rats," In: *New Directions in Research and Clinical Works for Obesity and Diabetes Mellitus*, Eds. Sakamoto, M., Angel, A., Hotta, N., pp. 197–203. Elsevier (1991).

Sukuzi, S. et al., "Urinary–chiro–Inositol Excretion is an Index Marker of Insulin Sensitivity in Japanese Type II Diabetes," 17(12) *Diabetes Care* 1465–1468 (1994).

United Kingdom Prospective Diabetes Study, "United Kingdom Prospective Diabetes Study (UKPDS) 13: Relative Efficacy of Randomly Allocated Diet, Sulphonylurea, Insulin or Metformin in Patients with Newly Diagnosed Non–Insulin Dependent Diabetes Followed for Three Years," 310 *BMJ* 83–88 (1995).

Varese, R.V. et al., "Insulin–induced Activation of Glycerol 3–Phosphate Acyltransferase by chiro–inositol–containing Insulin Mediator is Defective in Adipocytes of Insulin resistant, Type II Diabetic Goto–Kakizaki Rats," 91 *Proc. Natl. Acad. Sci.* 11040–11044 (1994).

Villar–Palasi, C. and Farese, R., "Impaired Skeletal Muscle Glycogen Synthase Activation by Insulin in the Goto–Kakizaki (G/K) Rat," 37 *Diabetologia* 885–888 (1994).

Walker, M., "Obesity, Insulin Resistance, and Its Link to Non–Insulin–Dependent Diabetes Mellitus," 44(9) (Suppl. 3) *Metabolism* 18–20 (1995).

Williams, B., "Insulin Resistance: The Shape of Things to Come," 344 *The Lancet* 521–524 (1994).

Williams, R. and Palmer, J., "Farewell to Phenformin for Treating Diabetes Mellitus," 83(4) *Annals of Internal Medicine* 567–568 (1975).

* cited by examiner

IPG A-TYPE MEASURED BY STIMULATION OF LIPOGENESIS
IPG P-TYPE MEASURED BY STIMULATION OF PDH PHOSPHATES

IPG A-TYPE MEASURED BY STIMULATION OF LIPOGENESIS
IPG P-TYPE MEASURED BY STIMULATION OF PDH PHOSPHATES

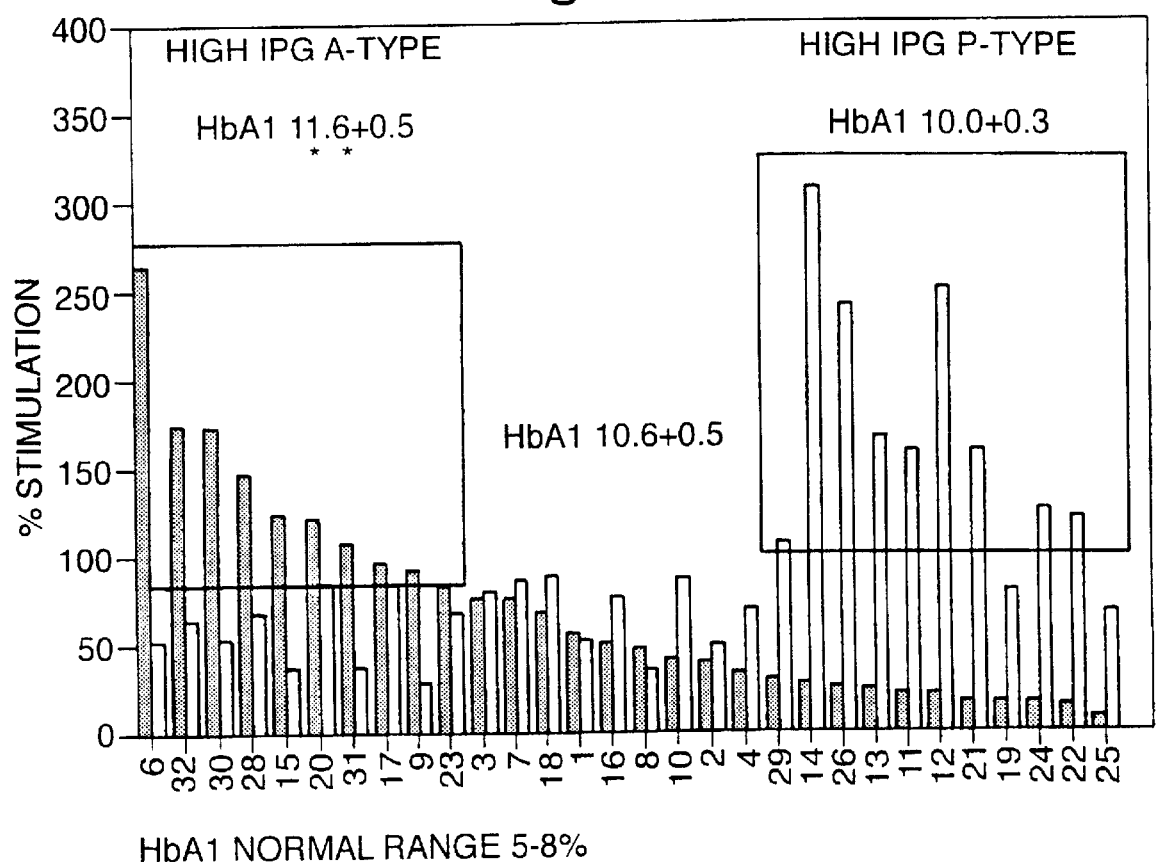

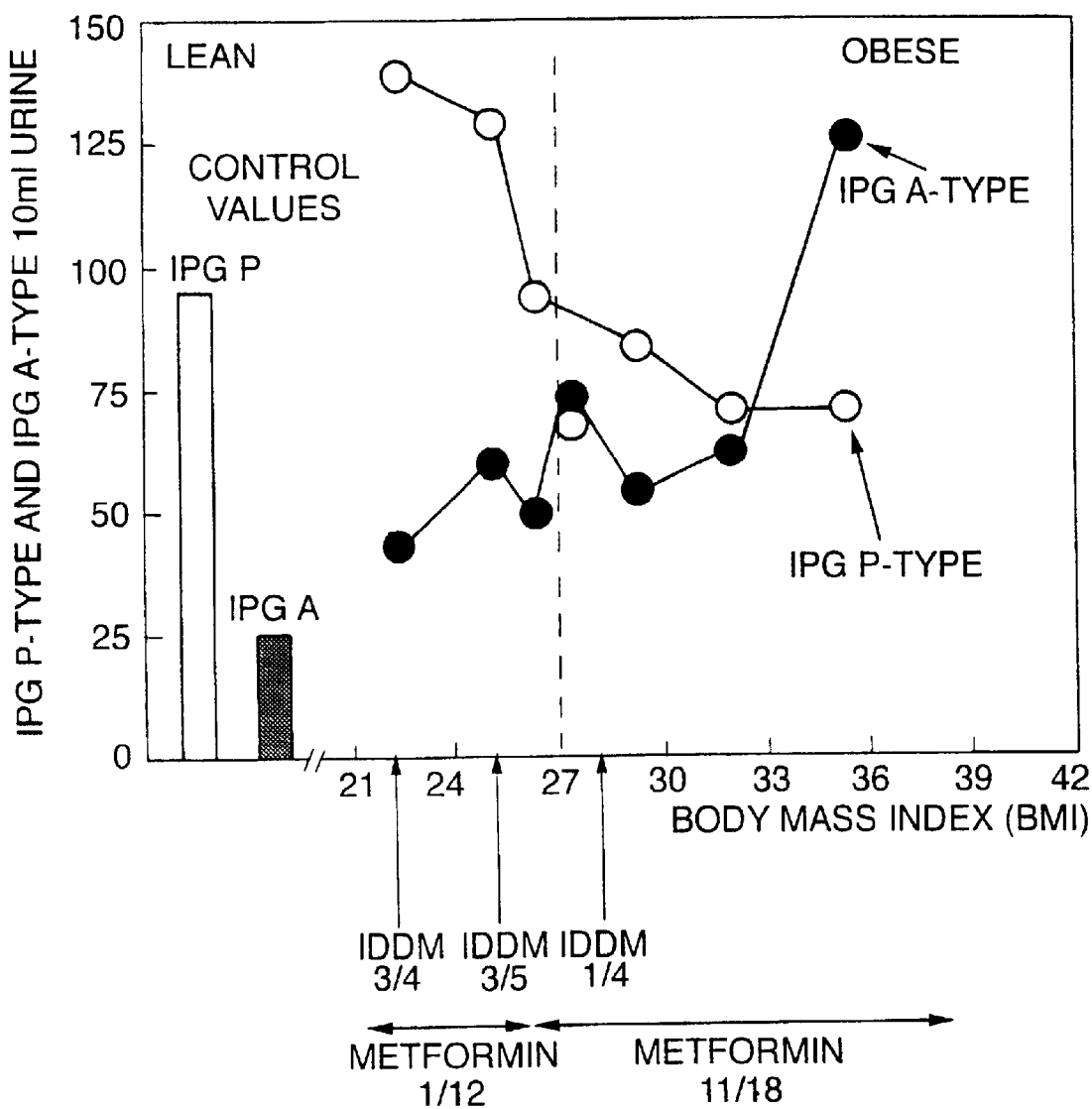

Fig. 5B.
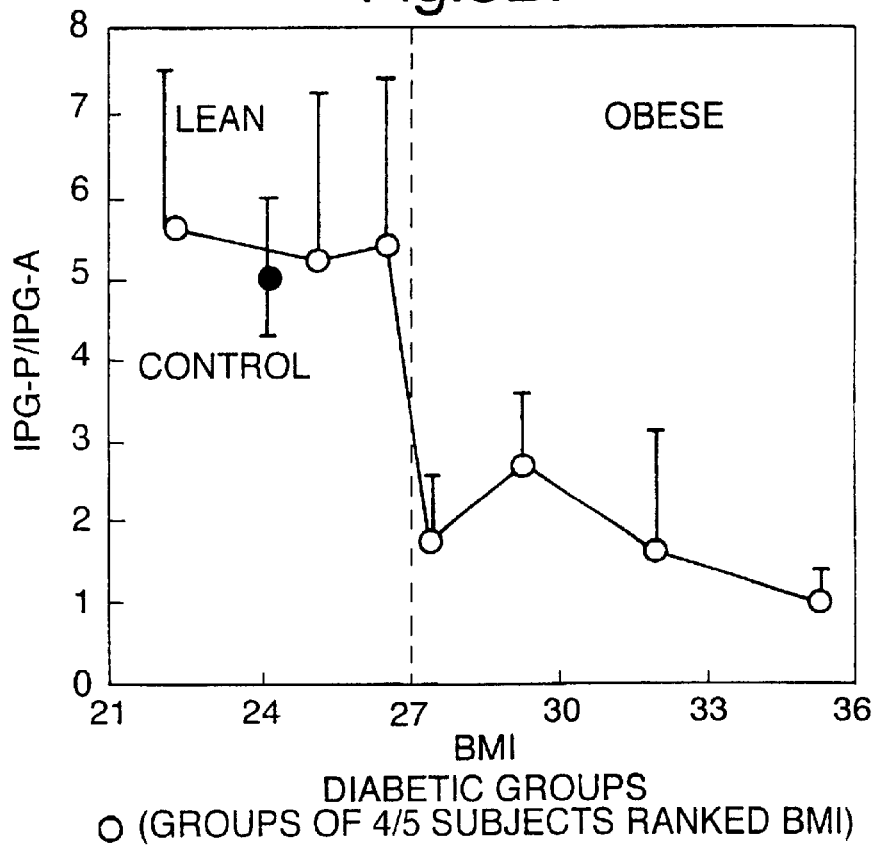
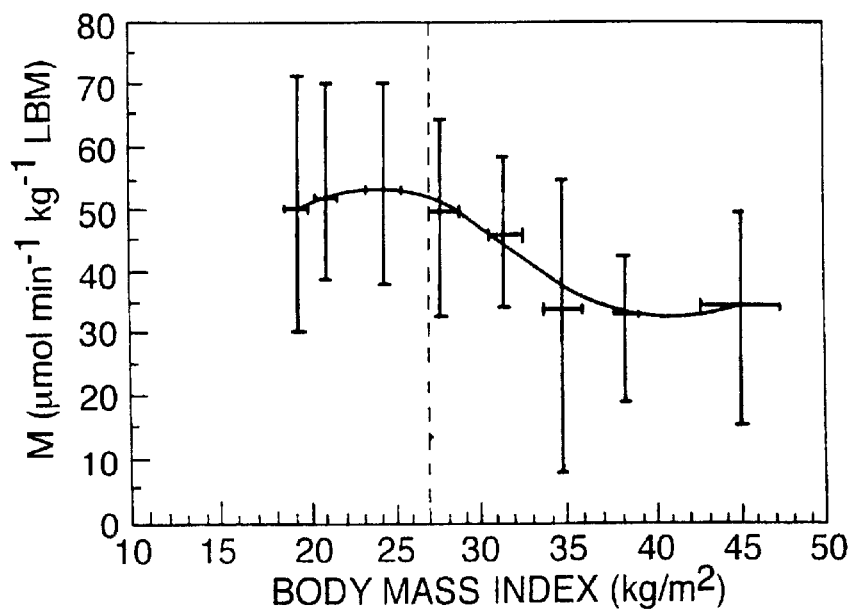
THE VERTICAL DOTTED LINE MARKS THE CONVENTIONAL
CUT-OFF FOR THE DEFINITION OF OBESITY (BMI > 27)

MATERIALS AND METHODS RELATING TO THE DIAGNOSIS AND TREATMENT OF DIABETES AND OBESITY

This application is a 35 USC 371 of PCT/GB97/02440, filed Sep. 11, 1997.

FIELD OF THE INVENTION

The present invention relates to materials and methods for the diagnosis and treatment of diabetes and associated obesity.

BACKGROUND OF THE INVENTION

Diabetes is said to affect about 5% of the world population. The etiology of the two major forms of diabetes, referred to as insulin-dependent diabetes (IDDM) and non-insulin dependent diabetes (NIDDM), is quite different despite similarities in their pathophysiologies. IDDM often arises in early life, and is due to autoimmune destruction of pancreatic β-cells resulting in partial or complete loss of β-cell function. NIDDM is more common in later life, typically more than 40 years in age, and about 85% of all diabetics have this form. While the NIDDM group is best regarded as a heterogeneous set of disorders, two major sub-groups are recognised, these are the non-obese, and the obese, with the latter being some 30% of the cases [1].

Some 60 years ago, Himsworth [2] first described the concept of variability in the sensitivity to insulin Insulin resistance, defined as the impaired sensitivity of the effects of insulin on whole body glucose utilization, has, as major components, the suppression of hepatic glucose production and the disposal of glucose loads by muscle via glycogen synthesis and glucose oxidation [3,4]. The importance of insulin resistance in the pathophysiology of NIDDM and the increased risk factors for vascular disease in insulin resistant individuals has been highlighted by Reaven [5,6], who described a cluster of risk factors under the term 'syndrome X' which included; glucose intolerance, high circulating insulin, disordered lipid metabolism and hypertension. The increased prevalence of NIDDM in developed countries together with its association with heart disease and stroke, makes this one of the most devastating diseases in the Western world.

It is, perhaps, surprising, despite the remarkable increase in our understanding of the complex signalling functions of insulin, of the cellular and molecular mechanisms that underlie the diverse actions of this hormone, and of the role of mutant insulin receptors in insulin resistance, that standard texts and recent review state that "The etiology and pathogenesis of the most frequent types of NIDDM, however, are not well defined" [1]; that "The mechanisms linking obesity and insulin resistance are not known" [7]; and that ". . . the search for the physiological, biochemical and molecular basis for cardiovascular risk factor clustering in syndrome X continues" [8].

SUMMARY OF THE INVENTION

A new insight into the understanding of insulin action and NIDDM has emerged from the identification and partial characterisation of two families of inositol phosphoglycans (IPGs), each exhibiting specific insulin-mimetic properties certain of which are shown in Table 1. The IPG A-type stimulate lipogenesis, inhibit cAMP-dependent protein kinase and modify the activity of adenylate cyclase and cAMP-phosphodiesterase, thus contributing to the control of cAMP and cAMP-regulated intracellular processes which are classically inhibited by insulin. The IPG P-type activate, among other enzymes, pyruvate dehydrogenase phosphatase (PDH P'ase), glycogen synthase phosphatase and glycerol 3-phosphate acyl transferase. The activation of key phosphoprotein phosphatases plays a major role in the regulation of the disposal of glucose by oxidative metabolism via PDH, and by the non-oxidative route of storage by glycogen synthesis, both pathways classically known to be regulated by insulin [see 9–12].

The reported occurrence of inositol phosphoglycans in a wide range of tissues, and the influence of insulin on their release both in vivo and in vitro [10,12,13], has led to an intense interest in the role these compounds might play in the pathogenesis of experimental, genetic and clinical form of diabetes. Evidence that these inositol-containing compounds are important in insulin signalling comes both from in vitro studies on isolated cells and in vivo measurements using animal models of IDDM (type-I) and NIDDM (type-II) diabetes, including the findings that:

(a) Addition of antibody with anti-IPG specificity is able to block both the metabolic and mitogenic actions of insulin [14, Rademacher et al, unpublished observations].

(b) Anti-IPG antiserum inhibits the stimulating effects of insulin and P-type IPG on adipocyte glycerol-3-phosphate acyltransferase in normal Wistar rats [15].

(c) Mutant cells unable to synthesize IPGs respond to insulin as determined by tyrosine phosphorylation, but are not stimulated to elicit at least some of the metabolic effects of the hormone, in particular glycogen synthesis [16].

(d) The glycans promote serine/threonine dephosphorylation in adipocyte extracts via a mechanism requiring protein phosphatase 1, the phosphatase that regulates the activity of both glycogen synthase and phosphorylase [16,17].

(e) Impairment of glycosyl-phosphatidyl inositol-dependent insulin signalling system in isolated rat hepatocytes by strepotozotocin-induced diabetes [18].

(f) Diabetic GK rats, recognised as a model for insulin-resistant type II diabetes [9], have a defect in synthesizing or releasing functional IPGs as shown by the impaired insulin-induced activation of glycerol-3-phosphate acyltransferase by a chiro-inositol-containing insulin mediator [15] and impaired skeletal muscle glycogen synthase activation by insulin [19].

(g) Infusion of chiro-inositol into normal rats given a glucose load, or to streptozotocin-diabetic rats, results in decreased plasma glucose and enhanced activity of glycogen synthase: positive effects of chiro-inositol treatment on insulin-resistant Rhesus monkeys have also been reported [20,21].

Evidence that IPGs are important in the pathogenesis of human insulin-resistant type II diabetes derives largely from studies in which two basic approaches have been used (see Table 2):

(a) Measurements of the free chiro- and myo-inositol content of urine of diabetic subjects using gas chromatography and mass spectrometry.

(b) Measurement of the bioactivity of inositol-phosphoglycan mediators in urine and tissue extracts employing bioassay procedures, e.g. activation of pyruvate dehydrogenase phosphatase, inhibition of cAMP-dependent protein kinase. The main findings from these studies are given in Table 2.

In summary:

(a) Free chiro-inositol. This was shown to be decreased in urine of NIDDM subjects by Kennington et al [22] and by Suzuki et al [23], and to be decreased in urine of spontaneously diabetic rhesus monkeys [24]. The decreased urinary excretion rate has been reported to be directly associated with insulin resistance in a number of studies in human patients [22,25]. In contrast, increased urinary concentrations of chiro-inositol were reported by Ostlune et al [26]. The discrepancies between these reports have not been resolved.

(b) IPG P-type. Decreases in urinary excretion levels, as well as decreased concentration of chiro-inositol-containing IPGs, were found in muscle biopsy samples and haemodialysates of diabetic patients [25].

(c) Free myo-inositol. This was reported to be increased in urine of NIDDM subjects in studies by Kennington et al [22] and by Ostlund et al [26].

(d) IPG A-type. Asplin et al [25] reported unchanged IPG A-Type in urine of NIDDM subjects using the bioassay system of inhibition of cAMP-dependent protein kinase.

Two other lines of work give further support to the concept that IPGs play a significant role in the insulin signal transduction system in diabetic patients.

(a) The report that increased plasma levels of chiro-inositol were found in diabetic patients treated with insulin [Ostlund et al 26].

(b) Studies by Prochazha et al [27] on the genetic basis for insulin resistance in Pima Indians, centred on the genetic analysis of protein phosphatase 1 (PP1), a key regulatory enzyme in glycogen synthesis. Their conclusion that the structural gene for PP1 catalytic b subunit does not appear to be a major genetic determinant responsible for PP1 abnormalities, lends further support to the concept of a key role for inositol-containing phosphoglycans in the aetiology of insulin resistance and disordered glycogen metabolism.

In view of: (i) the growing body of evidence pointing to the importance of the inositol phosphoglycans in insulin action and disorders of insulin response in NIDDM, (ii) the key role IPG P-type and IPG A-type play in the regulation of enzymes involved in disposal of glucose by oxidative and non-oxidative routes, in the regulation of lipogenesis, triacylglycerol formation and lipolysis, and in glaconecogenesis, (iii) the divergent and meagre data on the bioactive species of IPG P-type and IPG A-type in urine; it was deemed important to make a detailed study of the relationship between urinary IPGs and NIDDM in a cross-sectional study of spot urine samples from a randomised series of male diabetic patients, (iv) studies on the measurement in urine of chiro and myo-inositol have been complicated by the fact that both breakdown of endogenous IPGs and dietary sources of the sugars will be present. Thus, prior art studies in this area which assumed that the P-type mediator contains chiro-inositol and that the A-type mediator contains myo-inositol must be interpreted with caution, see Fonteles, M C, Huang, L C, Larner, J, Diabetologia, 39:731–734, (1996), in which the authors report that they incorrectly identified the inositol in the P-type mediator which is pinitol and not chiro-inositol. As pinitol is not converted to chiro-inositol by the acid conditions used in carbohydrate analysis, this is an example of misidentification in this area.

This invention arises from the discovery, as detailed below, of a correlation between levels of A-type and P-type IPGs, and the ratio of P-type to A-type, and the occurrence of certain forms of diabetes and obesity.

The present invention provides, inter alia:

(1) Diagnosis of type II diabetes (NIDDM) by measuring the ratio of P-type:A-type mediators in blood or urine.

(2) Treatment of IDDM or lean type II diabetes (NIDDM) (BMI<27) with a mixture of P- and A-type mediators.

(3) Treatment of obese type II diabetes (NIDDM) with a P-type mediator and/or an A-type antagonist.

A therapeutic treatment for type II obese diabetics comprises administering an antagonist to A-type IPG. We show herein (see FIG. 5B) that male obese type II diabetics release a 2:1 unit ratio of P:A mediators. The A-type drives glucose into fat while the P-type drives glucose into glycogen for energy consumption. In the type II diabetics, insulin stimulates the release of 6 units of P-type for every 3 units of A-type. In contrast for lean diabetics or type I (insulin deficient) or control patients insulin stimulates the release of 6 units of P-type for every one unit of A-type. The obese diabetics therefore drive three times as much glucose into fat as the normal controls or lean diabetics. 80% of blood glucose is normally taken up by muscle which is a P-type responsive tissue. In the type II diabetics, less goes into muscle and more into fat, but removal by fatty tissue is less efficient and consequently the blood glucose levels rise, giving rise to the diabetic state. These patients normally are then hyperinsulinaemic which pushes more glucose into the fat compounding the problem and setting up a vicious cycle.

For treatment of type I diabetes, about a 6:1 mixture of P:A mediators can be used in males, and about a 4:1 mixture in females.

Accordingly, in a first aspect, the present invention provides a method of diagnosing diabetes, the method comprising determining the level or ratio of P- and/or A-type inositolphosphoglycans (IPGs) in a biological sample from a patient. The determination of this ratio helps to accurately assign the patient to a diabetic group, allowing the treatment of diabetes in the patient to be tailored accordingly to that group and/or the patient's individual needs, e.g. by then administering to the patient appropriate amounts of P- or A-type IPGs, or their antagonists, to correct the levels and/or ratio of these compounds in the patient.

In one embodiment, the method of diagnosing diabetes comprises the steps of:

(a) contacting a biological sample obtained from the patient with a solid support having immobilised thereon a first binding agent having binding sites specific for one or more P-type IPGs and a second binding agent having binding sites for one or more A-type IPGs;

(b) contacting the solid support with one or more labelled developing agents capable of binding to unoccupied binding sites, bound IPGs or occupied binding sites; and, (c) detecting the label of the developing agents specifically binding in step (b) to obtain values representative of the levels of the P- and A-type IPGs in the sample.

Preferably, the method comprises the further step of:

(d) using the values to obtain a ratio of the P- and A-type IPGs in the sample.

Additionally or alternatively, the levels of the P- and/or A-type IPGs in a sample, and hence their ratio, can be determined using one or more of the assays for P- and A-type biological activity described below.

In a further aspect, the present invention provides the use of P- or A-type inositolphosphoglycans (IPGs), or antagonists to P- or A-type IPGs, in the preparation of a medicament for the treatment of diabetes.

In one embodiment, the present invention provides the use of an A-type IPG antagonist and/or a P-type IPG in the preparation of a medicament for the treatment of obese type II diabetes. As described above, these patients have a form of diabetes characterised by an reduced ratio of P:A-type IPGs.

In a further embodiment, the present invention provides the use of P-type and A-type IPGs in the preparation of a medicament for the treatment of IDDM or lean type II diabetes (NIDDM). In this embodiment, preferably, the P:A-type ratio is about 6:1 mixture for male patients and about a 4:1 mixture for female patients. In this use, the P- and A-type IPGs can be administered to the patient separately or formulated together for administration. As mentioned above, it is expected that formulations will be tailored to each individual patient depending on the levels or ratio of the IPGs in the patient. The formulations may be tailored by the physician or by the patient at the time of administration.

In a further aspect, the present invention provides a pharmaceutical composition comprising an A-type IPG antagonist and/or a P-type IPG in combination with a pharmaceutically acceptable carrier.

In a further aspect, the present invention provides a pharmaceutical composition comprising a mixture of P- and A-type IPGs in combination with a pharmaceutically acceptable carrier.

In a further aspect, the present invention provides a kit for treating obese type II diabetes comprising a first container of P-type IPG and a second container of A-type IPG antagonist, for simultaneous or sequential administration.

In a further aspect, the present invention provides a method of screening for P- or A-type IPG antagonists, the method comprising:

(a) contacting a candidate antagonist and a P- or A-type IPG in an assay for a biological property of the P- or A-type IPG under conditions in which the IPG and the candidate antagonist can compete;

(b) measuring the biological property of the IPG; and, (c) selecting candidate antagonists which reduce the biological activity of the IPG.

The present invention will now be described by way of example and not by limitation with reference to the accompanying drawings.

BRIEF DESCRIPTION OF THE DRAWINGS

FIG. 2 shows the IPG A- and IPG P-type content of urine from diabetic subjects showing high IPG A-type and high IPG P-type groups with their HbA1 values.

FIG. 5 shows (A) the relationship between IPG A-type and IPG B-type and body mass index in diabetic subjects, (B) the ratio of IPG A-type:IPG B-type as a function of body mass index, and insulin sensitivity (M value)as a function of body mass index. In (A), the diabetic subjects were divided into 7 groups according to their body mass index (BMI–kgm$^2$). The average values for the IPG A-type (•-•) and the IPG P-type (o-o) for each subgroup are shown. The average values for the IPGs of the control group are shown by vertical columns. The BMI of the control group was 24±2.4 (mean±SD). The arrows and numbers along the abscissa show the number of diabetic subjects in each group receiving either insulin treatment or metformin with or without other treatments. Metformin is the treatment of choice for overweight and obese NIDDM subjects. In (B) the vertical dotted line marks the conventional cut-off for the definition of obesity (BMI>27).

DETAILED DESCRIPTION OF THE INVENTION IPGs

Figure 1A:
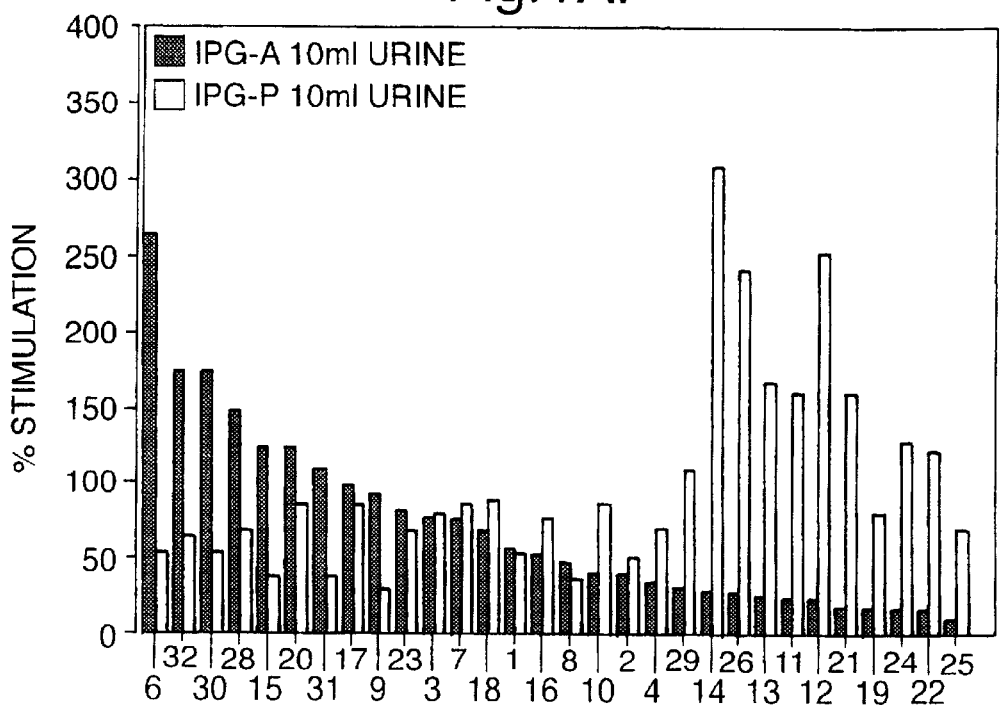
FIG. 1A shows a graph of IPG A- and IPG P-type content of urine from diabetic subjects (arranged in order of IPG A-type content).

Studies have shown that A-type mediators modulate the activity of a number of insulin-dependent enzymes such as cAMP dependent protein kinase (inhibits), adenylate cyclase (inhibits) and cAMP phospho-diesterases (stimulates). In contrast, P-type mediators modulate the activity of insulin-dependent enzymes such as pyruvate dehydrogenase phosphatase (stimulates) and glycogen synthase phosphatase (stimulates). The A-type mediators mimic the lipogenic activity of insulin on adipocytes, whereas the P-type mediators mimic the glycogenic activity of insulin on muscle. Both A- and P-type mediators are mitogenic when added to fibroblasts in serum free media. The ability of the mediators to stimulate fibroblast proliferation is enhanced if the cells are transfected with the EGF-receptor. A-type mediators can stimulate cell proliferation in the chick cochleovestibular ganglia.

Soluble IPG fractions having A-type and P-type activity have been obtained from a variety of animal tissues including rat tissues (liver, kidney, muscle brain, adipose, heart) and bovine liver. A- and P-type IPG biological activity has also been detected in human liver and placenta, malaria parasitized RBC and mycobacteria. The ability of an anti-inositolglycan antibody to inhibit insulin action on human placental cytotrophoblasts and BC3H1 myocytes or bovine-derived IPG action on rat diaphragm and chick ganglia suggests cross-species conservation of many structural features. However, it is important to note that although the prior art includes these reports of A- and P-type IPG activity in some biological fractions, the purification or characterisation of the agents responsible for the activity is not disclosed.

In co-pending patent applications claiming priority from GB-A-9618930.3 and GB-A-9618929.5, we have described the isolation and characterisation of P-type and A-type IPGs.

A-type substances are cyclitol-containing carbohydrates, also containing $Zn^{2+}$ ion and optionally phosphate and having the properties of regulating lipogenic activity and inhibiting cAMP dependent protein kinase. They may also inhibit adenylate cyclase, be mitogenic when added to EGF-transfected fibroblasts in serum free medium, and stimulate lipogenesis in adipocytes.

P-type substances are cyclitol-containing carbohydrates, also containing $Mn^{2+}$ and/or $Zn^{2+}$ ions and optionally phosphate and having the properties of regulating glycogen metabolism and activating pyruvate dehydrogenase phosphatase. They may also stimulate the activity of glycogen synthase phosphatase, be mitogenic when added to fibroblasts in serum free medium, and stimulate pyruvate dehydrogenase phosphatase.

In view of the optional presence of phosphate in the A- and P-type IPGs, references to "inositolphosphoglycans" or "IPGs" include compounds in which phosphate is not present. These compounds are alternatively be termed inositolglycans (IGs).

The A- and P-type substances were also found to have the following properties:
1. Migrates near the origin in descending paper chromatography using 4/1/1 butanol/ethanol/water as a solvent.
2. The substances contains phosphate which is directly related to activity.
3. The free GPI precursors are resistant to cleavage by GPI-PLC.
4. They are bound on Dowex AG50 (H+) cation exchange resin.
5. They are bound on an AG3A anion exchange resin.
6. The activity is resistant to pronase.
7. They are detected using a Dionex chromagraphy system.
8. The P-type substance is partially retained on C-18 affinity resin.

The A- and P-type substances may be obtained from human liver or placenta by:

(a) making an extract by heat and acid treatment of a liver homogenate, the homogenate being processed from tissue immediately frozen in liquid nitrogen;

(b) after centrifugation and charcoal treatment, allowing the resulting solution to interact overnight with an AG1-X8 (formate form) anion exchange resin;

(c) collecting a fraction having A-type IPG activity obtained by eluting the column with 50 mM HCl, or a fraction having P-type IPG activity obtained by eluting the column with 10 mM HCl;

(d) neutralising to pH 4 (not to exceed pH 7.8) and lyophilising the fraction to isolate the substance.

(e) descending paper chromatography using 4/1/1 butanol/ethanol/water as solvent.

(f) purification using high-voltage paper electrophoresis in pyridine/acetic acid/water.

(g) purification using Dionex anion exchange chromatography, or purification and isolation using Vydac 301 PLX575 HPLC chromatography.

More details of the methods for obtaining these IPGs are provided in the said patent applications, the contents of which are incorporated herein by reference.

Antagonists

As mentioned above, P-type or A-type IPG antagonists include substances which have one or more of the following properties:

(a) substances capable of inhibiting release of the P- or A-type mediators;

(b) substances capable of reducing the levels of P- or A-type IPG via an IPG binding substance (e.g. an antibody or specific binding protein); and/or, (c) substances capable of reducing the effects of P- or A-type IPGs.

In one embodiment, the IPG antagonists are specific binding proteins. Naturally occurring specific binding proteins can be obtained by screening biological samples for proteins that bind to IPGs.

In a further embodiment, the antagonists are antibodies capable of specifically binding to P- or A-type IPGs. The production of polyclonal and monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. A hybridoma producing a monoclonal antibody may be subject to genetic mutation or other changes, which may or may not alter the binding specificity of antibodies produced.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The antibodies described above may also be employed in the diagnostic aspects of the invention by tagging them with a label or reporter molecule which can directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

In a further embodiment, the IPG antagonists are synthetic compounds. These may be produced by conventional chemical techniques or using combinatorial chemistry, and then screened for IPG antagonist activity. These compounds may be useful in themselves or may be used in the design of mimetics, providing candidate lead compounds for development as pharmaceuticals. Synthetic compounds might be desirable where they are comparatively easy to synthesize or where they have properties that make them suitable for administration as pharmaceuticals, e.g. antagonist which are peptides may be unsuitable active agents for oral compositions if they are degraded by proteases in the alimentary canal. Mimetic design, synthesis and testing is generally used to avoid randomly screening large number of molecules for a target property.

Production of Monoclonal Antibodies

Inositolphosphoglycan (IPG) purified from rat liver by sequential thin layer chromatography (TLC) was used to immunize New Zealand rabbits and Balb/c mice by using conventional procedures.

After immunisation, monoclonal antibodies were prepared using the approach of fusion of mouse splenocytes ($5\times10^6$ cells/ml) with mutant myeloma cells ($10^6$ cells/ml). The myeloma cell lines used were those lacking hypoxanthine-guanine phosphoribasyl transferase. The screening method of hybridoma cells was based on a non-competitive solid-phase enzyme immunoassay in which the antigen (IPG) was immobilised on a solid phase. Culture supernatant were added and positive hybridoma cells were selected.

A single cell cloning was made by limiting dilution.

Hybridomas for three monoclonal antibodies (2D1, 5HG and 2P7) were selected. All monoclonal antibodies were determined to be IgM using a EK-5050 kit (Hyclone).

In order to test that all monoclonal antibodies recognised IPGs, a non-competitive solid-phase enzyme immunoassay was used. F96 Polysorp Nunc-Immuno Plates are used for the assay. The polysorp surface is recommended for assays where certain antigens are immobilised.

The immobilised antigen (IPG) diluted to 1:800 captured the monoclonal antibody from tissue culture supernatant, ascitic fluid, and when the purified monoclonal antibody was used.

The detection method used an anti-mouse IgM, biotinylated whole antibody (from goat) and a streptavidin-biotinylated horseradish peroxidase complex (Amersham), ABTS and buffer for ABTS (Boehringer Mannheim).

The same immunoassay was used to evaluate the polyclonal antibody. In this assay, the detection method employed an anti-rabbit Ig, biotinylated species—specific whole antibody (from donkey).

The antibodies can be purified using the following method. Fast Protein Liquid Chromatography (Pharmacia FPLC system) with a gradient programmer GP-250 Plus and high precision pump P-500 was used in order to purify a polyclonal IPG antibody.

A HiTrap protein A affinity column was used for purification of polyclonal IPG from rabbit serum. Protein quantitation was made using a Micro BCA protein assay reagent kit (Pierce).

Monoclonal IgM antibodies were purified in two steps. Ammonium sulfate precipitation was the method chosen as a first step. Tissue culture supernatant was treated with ammonium sulfate (50% saturation). Pellet diluted in PBS was transferred to dialysis tubing before the second step.

Since ammonium sulfate precipitation is not suitable for a single step purification, it was followed by gel filtration chromatography-antibody solution in PBS run into a Pharmacia Sepharose 4B column. Protein quantitation was made reading the absorbance at 220–280 nm in a Perkin-Elmer lambda 2 UV/VIS spectrophotometer.

Protocol for Sandwich ELISA

The protocol below sets out an indirect, non-competitive, solid-phase enzyme immunoassay (sandwich ELISA) for the quantification of inositolphosphoglycans (IPG) in biological fluids, such as human serum.

In the assay, monoclonal IgM antibodies are immobilised on a solid phase. Tissue culture supernatant, ascitic fluid from mice with a peritoneal tumour induced by injecting hybridoma cells into the peritoneum and purified monoclonal antibody have been used in the immunoassay. F96 Maxisorp Nunc-Immuno plates were used for these assays. Maxisorp surface is recommended where proteins, specially glycoproteins such as antibodies, are bound to the plastic.

The immobilised antibody captures the antigen from the test sample (human serum or IPG used like a positive control).

A bridging antibody (a purified polyclonal IPG antibody from rabbit) is needed to link the anti-antibody biotinylated to the antigen.

The detection method employs an anti-rabbit Ig, biotinylated species-specific whole antibody (from donkey) and a streptavidin-biotinylated horseradish peroxidase complex (Amersham), ARTS and buffer for ABTS (Boehringer Mannheim).

The ELISA assay can be carried out as follows:
1. Add 100 $\mu$l/well in all the steps.
2. Add monoclonal antibody diluted 1:100 in PBS in a F96 Maxisorp Nunc-Immuno plate. Incubate at least 2 days at 4° C.
3. Wash with PBS three times.
4. Add a blocking reagent for ELISA (Boehringer Mannheim) in distilled water (1:9) 2 hours at room temperature.
5. Wash with PBS-Tween 20 (0,1%) three times.
6. Add a purified polyclonal antibody (diluted 1:100 in PBS), overnight at 4° C.
7. Wash with PBS-Tween 20 (0.1%) three times.
8. Add an anti-rabbit Ig, biotinylated species-specific whole antibody (from donkey) (Amersham) diluted 1:1000 in PBS, 1 h 30 min at room temperature.
9. Wash with PBS-Tween 20 (0.1%) three times.
10. Add a streptavidin-biotinylated horseradish peroxidase complex (Amersham) diluted 1:500 in PBS, 1 h 30 min at room temperature.
11. Wash with PBS three times.
12. Add 2.2-Azino-di-(3-ethylbenzthiazoline sulfonate (6)) diammonium salt crystals (ABTS) (Boehringer Mannheim) to buffer for ABTS (BM): Buffer for ABTS is added to distilled water (1:9 v/v). 1 mg of ABTS is added to 1 ml of diluted buffer for ABTS.
13. Read the absorbance in a Multiscan Plus P 2.01 using a 405 mm filter in 5–15 min.

Pharmaceutical Compositions

The mediators and antagonists of the invention can be formulated in pharmaceutical compositions. These compositions may comprise, in addition to one or more of the mediators or antagonists, a pharmaceutically acceptable excipient, carrier, buffer, stabiliser or other materials well known to those skilled in the art. Such materials should be non-toxic and should not interfere with the efficacy of the active ingredient. The precise nture of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition may be administered alone or in combination with other treatments, either simultaneously or sequentially dependent upon the condition to be treated.

Diagnostic Methods

Methods for determining the concentration of analytes in biological samples from individuals are well known in the art and can be employed in the context of the present invention to determine the ratio of P- and A-type inositol-phosphoglycans (IPGs) in a biological sample from a patient. This in turn can allow a physician to determine which of the sub-groups of diabetes a patient suffers from, and so optimise the treatment of it, in the case of type II obese diabetics, avoiding or ameliorating the symptoms of syndrome X. Examples of diagnostic methods are described in the experimental section below.

Preferred diagnostic methods rely on the determination of the ratio of P- and A-type IPGs. The methods can employ biological samples such as blood, serum, tissue samples or urine.

The assay methods for determining the concentration of P- and A-type IPGs typically employ binding agents having binding sites capable of specifically binding to one or more of the P or A-type IPGs in preference to other molecules. Examples of binding agents include antibodies, receptors and other molecules capable of specifically binding the IPGs. Conveniently, the binding agent(s) are immobilised on solid support, e.g. at defined locations, to make them easy to manipulate during the assay.

The sample is generally contacted with the binding agent(s) under appropriate conditions so that P-and A-type IPCs present in the sample can bind to the binding agent(s). The fractional occupancy of the binding sites of the binding agent(s) can then be determined using a developing agent or agents. Typically, the developing agents are labelled (e.g. with radioactive, fluorescent or enzyme labels) so that they can be detected using techniques well known in the art. Thus, radioactive labels can be detected using a scintillation counter or other radiation counting device, fluorescent labels using a laser and confocal microscope, and enzyme labels by the action of an enzyme label on a substrate, typically to produce a colour change. The developing agent(s) can be used in a competitive method in which the developing agent competes with the analyte for occupied binding sites of the binding agent, or non-competitive method, in which the labelled developing agent binds analyte bound by the binding agent or to occupied binding sites. Both methods provide an indication of the number of the binding sites occupied by the analyte, and hence the concentration of the analyte in the sample, e.g. by comparison with standards obtained using samples containing known concentrations of the analyte. In preferred embodiments, this can then be used to determine the P:A type ratio.

A. Objectives

In view of the potential importance of inositol phosphoglycans,(i) to the understanding insulin signal transduction systems, (ii) to the aetiology of insulin resistance, NIDDM and syndrome X, (iii) as a marker for the early detection of insulin-resistant diabetes, and (iv) as a potential therapeutic agent in NIDDM, a study has been undertaken to measure the urinary levels of inositol phosphoglycans in normal male subjects and in male diabetic patients, including IDDM, NIDDM (both lean and obese), using bioassay procedures in which the stimulation of well established systems, known to be activated by these insulin-mediators, were employed (see Experimental section below).

The concentration and ratio IPG P-type and IPG A-type in urine samples were determined, and comparison made with clinical data at the University College, London Hospitals, with a view to gaining information on the possible links between changes in IPGs and markers of the type and severity of diabetes. The clinical parameters included: $HbA_1$, urinary creatinine and protein, blood pressure, body mass index (weight kg/height $m^2$), complications (e.g. cardiovascular, renal, retinal, neurological), age and treatment. The duration of treatment at the hospital is known, but firm evidence of the total duration of diabetes is not always available or reliable, and has not been included here.

This cross-sectional study of a randomised selection of 30 diabetic subjects and approximately the same number of non-diabetic control male subjects will not reveal whether any correlations observed between clinical markers and changes in IPGs represent a cause, a consequence or a coincidence. Nevertheless, it is anticipated that the present data will provide:

(a) Additional information on the concentration of and direction of change of the bioactive urinary IPGs in diabetic male subjects—a matter of some controversy at this time;

(b) New information leading to a better understanding the biochemical basis of syndrome X;

(c) A starting point for consideration of the rationale of treatment of insulin resistant diabetics with IPGs.

B. Experimental

1. Assay of IPG A-type and IPG P-type Activity:

The activity of P- and A-type IPGs in urine extracts were studied using specific bioassay procedures. IPG P-type was determined using the activation of PDH phosphatase [28]. The PDH complex and PDH phosphatase (metal-dependent form) were prepared from beef heart as described by Lilley et al [28] and the assay of the activation of the phosphatase was performed by the spectrophotometric variant of the two-stage system described by these authors. This assay is considered to be a characteristic feature of IPG P-type (see Larner et al [29]). IPG A-type was determined by the stimulation of lipogenesis as measured by the incorporation of $[U-^{14}C]$ glucose into the lipids of adipocytes isolated from epididymal fat pads by the method of Rodbell [30]. A high degree of specificity for IPG A-type was found for this bioassay.

A straight line relationship between added IPGs and the stimulation of PDH phosphatase activity (IPG P-type) and lipogenesis in intact adipocytes (IPG A-type) was obtained; this relationship held at least up to a stimulation of +250%. These observations provided a basis for a unit to be defined and used for the purpose of comparison of yields of IPGs from different tissues and urine samples. Linearity between IPG added and the percentage change in response, has been observed by others (see Lilley et al [28] and Newman et al [31]), although Asplin et al [25] did not show linearity in their study on IPGs in human urine from normal and diabetic subjects, an effect which was particularly marked with the IPG A-type.

2. Extraction of IPG P-type and IPG A-type From Urine:

Urines were extracted as described by Asplin et al [25]. The final fractions were freeze dried and stored at −20° C. For use, the IPG fractions were resuspended in is water, immediately before assay, so that 10 µl of redissolved IPG corresponded to 10 ml urine. In view of the possibility that high, and varying, amounts of IPGs might be excreted in the different groups of subjects, and in order to ensure that the capacity of the resin was well in excess of the load applied, preliminary test runs were made to determine the optimal ratio of resin to starting urine volume. Linearity of recovery was obtained up to 100 ml urine per 18 g resin. In the present study, the ratio of 50 ml urine to 19 g resin Has maintained to allow for variation in IPG content.

3. Expression of Results:

A unit of IPG is defined as the amount causing a 50% activation in the basal level of the test system.

The yield of IPGs in urine is given on two different bases:

(i) Percentage stimulation of the test system by 10 µl final urine extract, allowing direct comparison with data of Asplin et al [15].

(ii) Units of IPG per 1 mmol creatinine.

The results are given as means±SEM, and as median values with the range of values.

4. Design of Experiment:

A cross-sectional study was undertaken with random spot samples collected at outpatients clinics. The patients included NIDDM subjects controlled by diet alone, by sulphonylureas, by metformin, by insulin or a combination of any of these treatments. Only a limited number of IDDM subjects were available. In the present survey, male subjects were used, this avoided complications arising from varying hormone profiles in women of different ages, in particular with or without HRT or contraceptive pills. The avoidance of a mix of male/female surveys was deemed important, since a separate study in this laboratory revealed that the IPG P-type/IPG A-type ratio was significantly lower urine from women than from men, largely Is- related to their higher IPG A-type concentration (see Table 3A). In addition to the measurement of IPG P-type and IPG A-type in urine the following clinical data was made available:

Urine: Creatinine, Protein

Blood: HbA1

Biodata: Age, weight and height (for calculation of BMI), blood pressure, complications (eg. cardiovascular, renal, neuropathy), ethnic origin.

Treatment: Insulin, sulphonyl ureas, biguanides, diet, (singly or combined).

The changes in inositol phosphoglycans in diabetes were correlated with the degree of glycaemic control as shown by HbA1, with obesity as indicated by basal metabolic index (BMI), with age and with blood pressure.

C. Results

1. Inositol Phosphoglycans in Urine of Diabetic and Control Subjects:

The concentration of IPG P-type and IPG A-type in urine of male diabetic subjects and non-diabetic controls are shown in Table 3A. The results are given as means±SEM and as median values together with their range. The most significant differences, taking the diabetic group as a composite whole, are the rise in IPG A-type and the unchanged IPG P-type in urine relative to the control group. These differences are significant both as concentration per ml urine and as units per mmol creatinine; the ration IPG P-type/IPG A-type fell in the diabetic group. The biodata relating to the diabetic and control subject is shown in Table 3B.

The present results contrast with those of Asplin et al [25], who reported, on the basis of a much smaller study, that IPG A-type was unchanged in NIDDM diabetes while IPG P-type decreased. These authors noted a non-linearity in their experiments in the dose response curve for IPG P-type (pH 2.0 fraction) measured by the stimulation of PDH phosphatase; such problems were not encountered in the study reported here. A further difference was in the bioassay systems used to measure IPG A-type, Asplin et al [25] employed the inhibition of cAMP-dependent protein kinase, wile the: present report is based on activation of lipogenesis by IPG A-type in isolated adipocytes.

Table 3A also includes data on the concentration of IPGs in the urine of non-pregnant women, a control group taken from a separate study on the urinary IPGs in pregnancy in normal, pre-eclamptic and diabetic women. The higher value for IPG A-type and for the lower value of the IPG P-type/IPG A-ratio for women relative to control male subjects are highly significant; in contrast the IPG P-type is substantially the same in both groups. These data underline the importance of separate assessment of the urinary IPGS in men and women in studying changes in diabetes (c.f. reports in [22], [25], [32]).

The heterogeneity of the underlying causes of diabetes, particularly in NIDDM [1,4,33–35], led to the re-examination of the data on the diabetic subjects to determine whether:

(a) There was a constant or varying relationship between the IPG A- and P types in diabetic subjects.

(b) Any correlation could be found between IPG profiles and markers of the degree of glycaemic control (HbA1) obesity, and hypertension, all factors of significance in relation to syndrome X.

(c) There was any correlation between treatments and IPG profile.

Figure 1B:
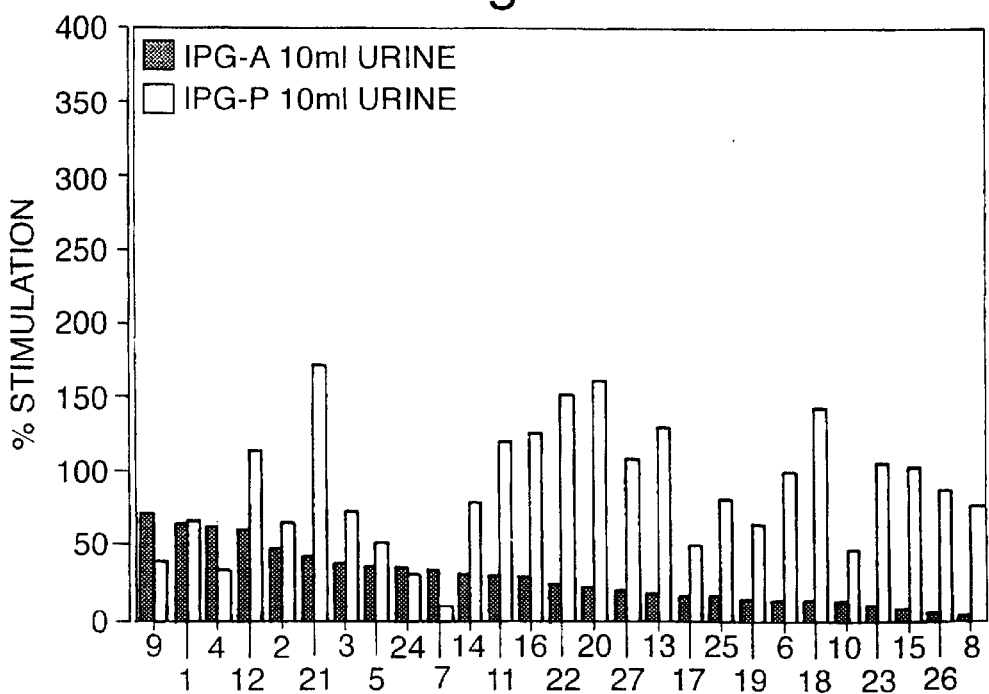
FIG. 1B shows a graph of IPG A- and IPG P-type content of urine from control subjects (arranged in order of IPG A-type content).

2. Relationships Between IPG A- and P-types in Diabetic Subjects:

Our first approach, in view of the highly significant change found in IPG A-type in urine of diabetic subjects, was to examine the results in descending order of the magnitude of this A-type (see FIG. 1A). It is clear that there are major differences across the series, both in the concentration of the A and P-types and in their ratios. Further, it appeared that there was a rough reciprocal relationship between these mediators, and that sub-groups could be distinguished which displayed either a high IPC, A-type/IPG P-type ratio or, conversely, had a high IPG P-type/IPG A-type ratio. There was a gradation across the series, and these extreme groups were separated by an intermediate group. The comparable data for the control group, similarly presented, is shown in FIG. 1B. It is clear that the control group has a narrower range of IPG concentration and presents as a more homogeneous sample without the extremes of high IPG A- or high IPG P-types seen in the diabetic groups. It is notable that the control subjects approximate to the intermediate group seen in the diabetic profile (FIG. 1A).

The differentiation of sub-groups within the diabetic subjects is further emphasised by outlining those values for IPG A-type or IPG P-type which are greater than values observed in the relatively homogeneous control non-diabetic group. These are shown, boxed in, for those subjects where the urinary IPG A-type or IPG P-type content is above the maximum control value (FIG. 2). The diabetic sub-groups so defined, as high IPG A-group and high IPG P-group, were considered to represent subjects outside the norm and to be worthy of special examination.

3. Correlation Between Markers of Diabetic Status and IPGs:

3.1 Relationship Between HbA1 and High IPG A—High IPG P-groups of Diabetics:

High values of HbA1, indicative of a sustained high is blood glucose levels, may be taken, as a first approximation, to be the net effect of glucose intake, hepatic production by gluconeogenesis and whole body utilization, and thus to be an index of glucose intolerance, a feature of syndrome X.

Figure 3A:
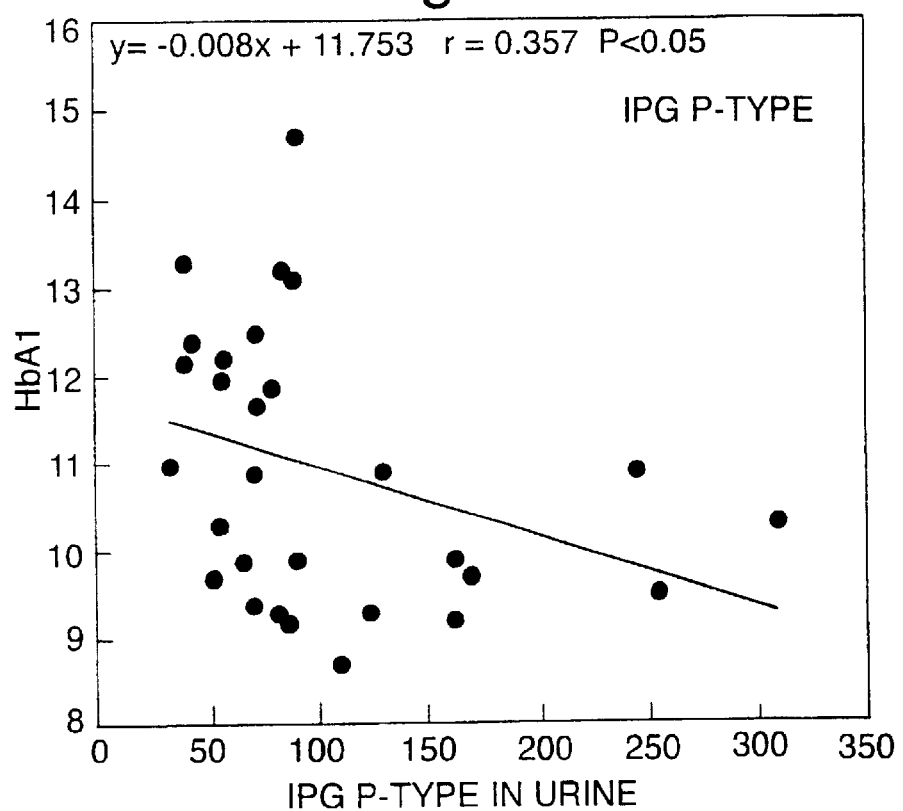
FIGS. 3A,B shows the correlation between IPG A-type and IPG P-type and HbA1.
Figure 3B:
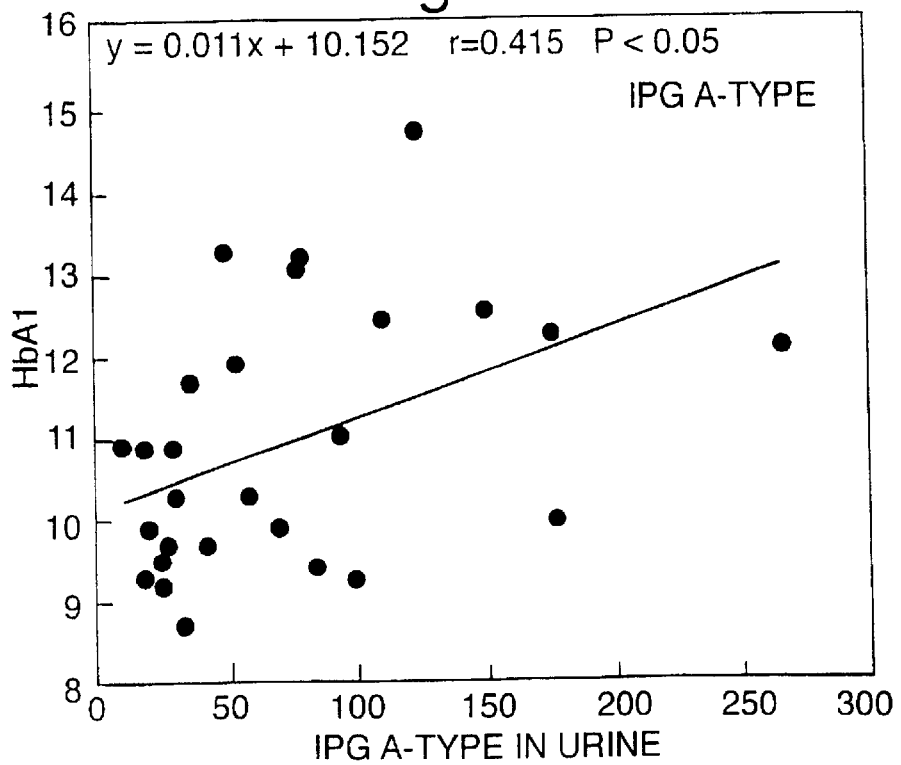

When the correlations between HbA1 and urinary concentrations of IPG A-type and IPG P-type were examined, a positive correlation was shown between HbA1 and urinary IPG A-type, contrasting with the negative correlation with IPG P-type; these relationships are shown in FIGS. 3A,B. The high IPG A-group was associated with a significantly raised HbA1 value of 11.6±0.5 (mean±SEM) while the high IPG P-group had a lower mean HbA1 value of 10.0±0.3, the difference between these two groups was significant ($P<0.01$) (see FIG. 2). From these results, it is suggested that diabetics with a high IPG A-type in the urine may exhibit one feature of syndrome X, namely glucose intolerance and a related insulin resistance. In contrast, diabetic subjects with a high IPG P value and a lower value for HbA1 might have a more effective rate of disposal of glucose via oxidative routes involving pyruvate dehydrogenase and storage via glycogen synthesis, and/or a decreased hepatic glucose production, all systems known to be regulated in part by IPG-type, thus having a better regulation of blood glucose, less intolerance to glucose and, in parallel, a lower HbA1.

3.2 Relationship Between Obesity (BMI) and IPG A-and P-types in Diabetes:

Two major subgroups of NIDDM are recognised, these are the obese and non-obese, with the latter being some 30% of the cases [1]. It was, therefore, of interest to examine whether the urinary IPGs in diabetic subjects showed any correlation with the degree of obesity as evaluated by the calculated body mass index. Subjects with values of BMI above 27 are held to be overweight, those over 30 to be obese [36].

Figure 4A:
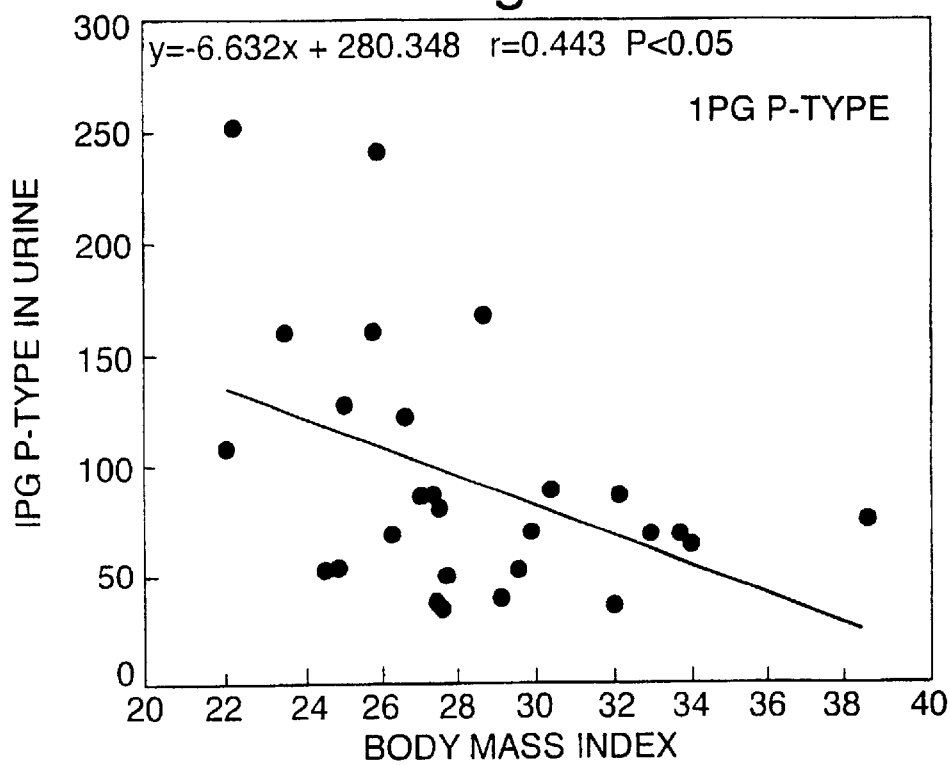
FIGS. 4A,B shows the correlation between IPG A-type and IPG B-type and body mass index.
Figure 4B:
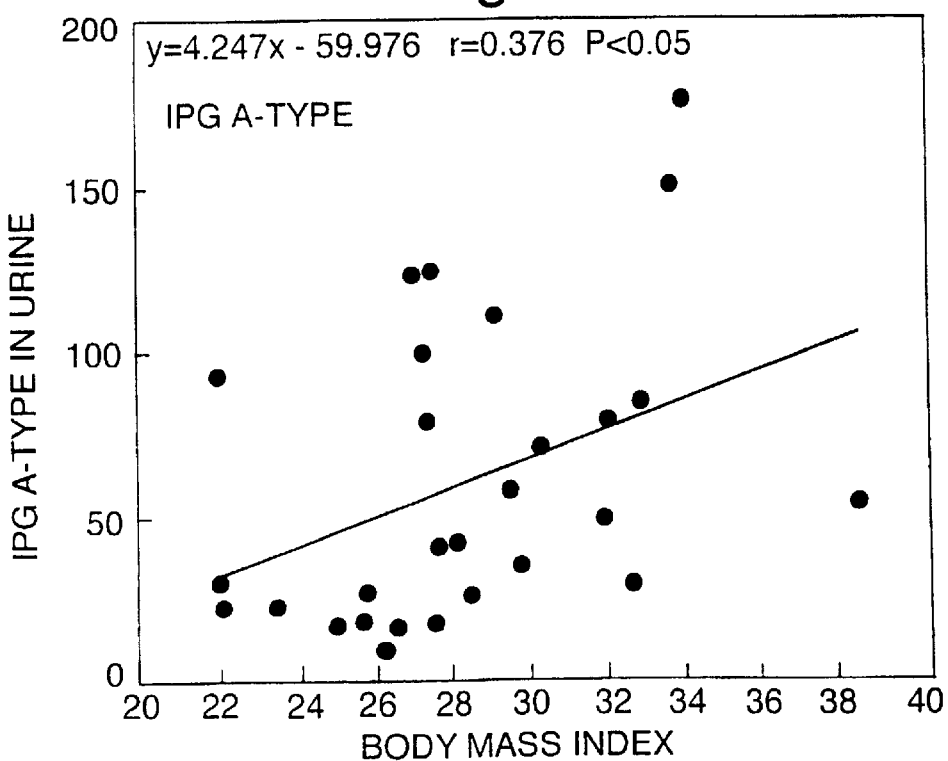

There was a strong negative correlation between urinary IPG P-type and BMI in diabetic subjects ($P,<0.01$) and a positive correlation with IPG A-type (FIGS. 4A,B). The profile of change is more clearly seen when groupings of 4 or 5 individuals, having closely similar BMI values, are shown, together with the concentration of urinary IPG A- and P-types and, in particular, when the data are presented as BMI versus the ratio of IPG P-type/IPG A-type. These results are presented in FIGS. 5A,B.

The most striking feature of these graphs is that lean subjects have a high IPG P-type and a low IPG A-type in urine, while the reverse is true for the obese subjects. Also significant is the observation that the curve for each of the IPGs cross-over at a value of the BMI about 27, the figure above which the clinicians consider a patient is overweight, patients with a BMI of 30 or more are classified as obese.

As indicated in FIG. 5A, 8 out of 9 patients treated with insulin, including the IDDM group and 3 NIDDM patients receiving insulin, fell within the normal or lean segment below the cut-off at a BMI value of 27. The majority of diabetic patients with a BMI value above 27 were receiving treatment with metformin, with or without other drugs or diet; this reflects the preferred treatment of overweight or obese diabetic patients with the biguanide, metformin [37, 38].

The clinical significance of the present results given 5 in FIG. 5A is further emphasised when compared with data from the literature [36], also shown in FIG. 5B. The survey reported by Ferrannini [36] compares the rate of glucose utilization by muscle to BMI in normal and obese patients, and show the well-established cross-over at 27, clearly relating a depressed rate of glucose utilization to obesity. Linking data from these two figures (FIGS. 5A,B), it is postulated that the rate of glucose utilization by muscle is related to the IPG P- to A-type ratio. This leads to the important conclusion that the degree of Is glucose intolerance in obese NIDDM subjects may be directly related to the profile of IPGs, a low P-type being associated with both obesity and less well controlled blood glucose values.

Figure 6A:
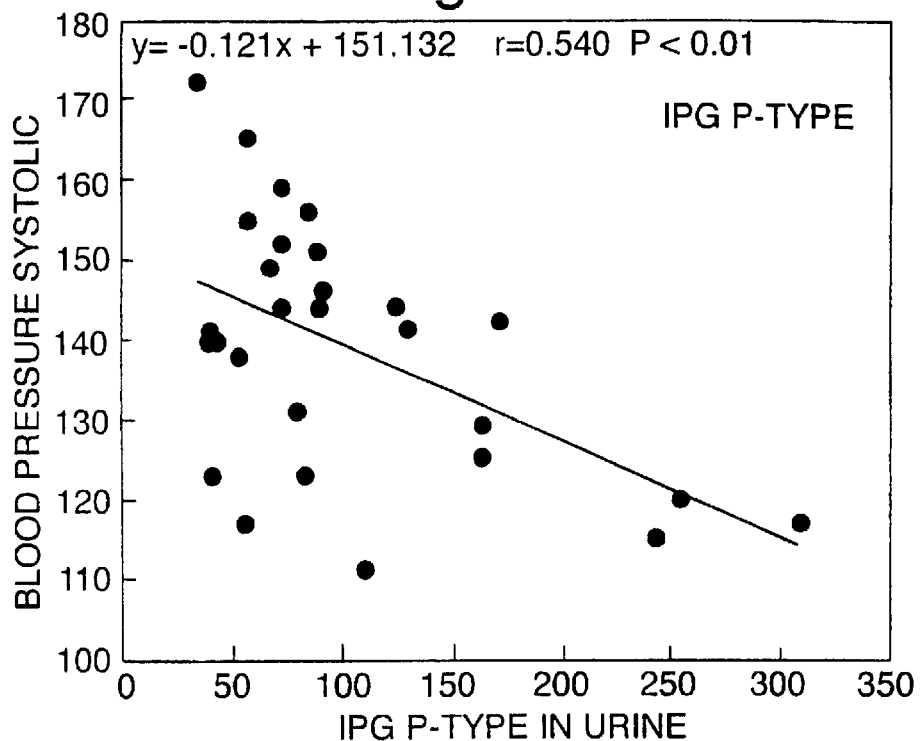
FIGS. 6A,B shows the relationship between systolic blood pressure and urinary IPG A- and P-types in diabetic (IDDM and NIDDM) subjects.
Figure 6B:
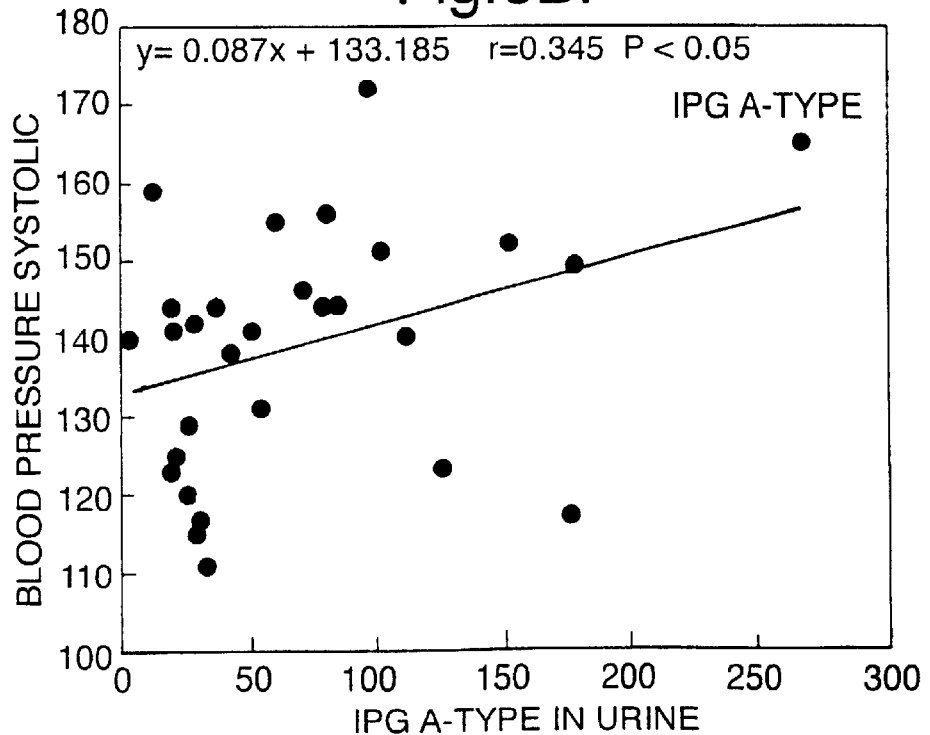

3.3 Relationship Between Hypertension and IPG A- and P-types in Diabetes:

The individual values for systolic blood pressure versus the concentration of the two types of IPG are shown in FIGS. 6A,B, from which it can be seen that those subjects with the highest blood pressure had the lowest IPG P-value, while those with a normal systolic blood pressure, of around 120, had IPG P values within the normal range (FIG. 6A). Conversely, there is a positive correlation between IPG A and systolic pressure (FIG. 6B). Both correlations are significant.

Since systolic blood pressure is correlated both with age and, as shown in the present study, with urinary IPG P-type, it was necessary to demonstrate that age was not a confounding factor in the IPG P-type/blood pressure association. An analysis by simple partial correlation demonstrated that there was a significant correlation between IPG P-type and blood pressure independent of the age factor.

D. Discussion

1. Urinary Levels of Bioactive Forms of IPGs in Diabetes:

The present cross-sectional survey of the bioactive forms of inositol phosphoglycans in the urine of male IDDM and NIDDM patients advances knowledge of the relationships between IPGs and clinical diabetes by providing evidence for an association between IPG P-type and IPG A-type concentrations and ratios, and degree of glycaemic control, systolic blood pressure, obesity and treatment. Differences between male and female non-diabetic control subjects were also recorded.

A significant correlation between urinary chiro-inositol excretion and in vivo insulin resistance has been reported in clinical surveys [32,40], in type II diabetic Rhesus monkeys [22] and in the GK rat model of type II diabetes [23]. The association between insulin resistance and obesity has also been clearly established [36]. Thus, the present observation that a low IPG-P/IPG-A ratio, is associated with obesity in NIDDM patients is entirely in keeping with the concept of the importance of IPG A-type and obesity. The differences between the present data and reported surveys [32] emphasise the importance of the use of biological assay systems to determine the links between inositol phosphoglycans and pathophysiological changes.

In a recent review Craig et al [32], stated that there was no significant correlation between glycated haemoglobin concentrations and urinary concentrations of chiro-inositol in a group of type II diabetic patients as a whole. The present work demonstrates a significant positive correlation between HbA1 and IPG A-type, and a negative correlation with IPG P-type in urine (FIGS. 3A,B). The boxed data in FIG. 2 highlights the group with an association of a high IPG-A/IPG-P ratio and poor metabolic control as revealed by HbA1.

It must be stressed that it may be even more important in attempting to relate changes in this putative mediator to diabetic status, to determine urinary IPG A-type by a bioassay system, rather then by myo-inositol excretion data, since myo-inositol is a product of the glucuronic acid cycle in kidney, a metabolic route known to be increased in experimental diabetes in the kidney and this would be further enhanced by renal growth in early diabetes [41].

If the relationships between obesity, raised HbA1 (values>11) and a low IPG P-type and/or low IPG-P/IPG-A ratio are confirmed in a more extensive study, then a basis for initial screening of patients with possible deficiencies in this putative second messenger system will have been identified, based on routine clinical monitoring of patients on attendance at clinic.

2. Inositol Phosthoglycans and Syndrome X:

The correlations shown between urinary IPG P-type and IPG A-type and HbA1, obesity and blood pressure in diabetic subjects provides a basis for speculation on the links between inositol phosphoglycans and syndrome X in NIDDM (Table 4). Any such speculation starts with the premise that the concentration of urinary IPGs are an indicator of circulating levels of these insulin mediators, and, thus that a low urinary IPG-P/IPG-A, or conversely high IPG-A/IPG-P, ratio is mirrored in the plasma levels and indicates the changes in the milieu interieur to which organs and tissues are exposed.

In summary, as shown in Table 5, section A, it is proposed that the switch over form the high P to A ratio in normal subjects and lean diabetics to a low P/A ratio in obese NIDDM patients is a critical factor in the obese syndrome. The expected effect of a low IPG P-type on aspects of glucose metabolism, based on the known effects of this putative insulin mediator on enzyme systems, is shown in section B. These include: (i) a decrease in glucose conversion to glycogen, (ii) a depressed pyruvate oxidation, and (iii) an increased hepatic production of glucose and (iv) increased hepatic glucose 6-phosphatase. Together, these changes will depress the ability of muscle to dispose of a glucose load, a major disturbance as muscle normally accounts for some 70% of glucose utilisation. This effect, together with a failure to suppress hepatic gluconeogenesis and glucose 6-phosphatase, would contribute to elevated blood glucose levels and glucose intolerance, key features of syndrome X.

The parallel effect of a high prevailing IPG A-type would be to compound the effects of the low IPG P-type described above (Table 5, section C). Firstly, IPG A-type stimulates lipogenesis in adipocytes and activates acetyl CoA carboxylase, thus increasing lipid synthesis. is Secondly, by inhibition of hormone-induced lipolysis, as a resultant effect of damping down the cAMP response, a raised IPG A-type would be expected to drive the balance between lipogenesis and lipolysis towards lipid synthesis and storage, contributing to obesity and disordered lipid metabolism, again a feature of syndrome X. An ancillary factor in the dyslipidemias of insulin-resistant NIDDM individuals may reside in the diminished adrenal function in diabetes [42], an effect which may be linked to altered cAMP regulation.

The role of IPGs in activating phosphatases involved in the regulation of pyruvate dehydrogenase, and glycogen synthesis IPG P-type, and in the regulation of cAMP linked systems, via the inhibition of cAMP-dependent protein kinase and adenylate cyclase, and activation of low Km cAMP phosphodiesterase, thus exerting a controlling influence on hormone-induced cAMP accumulation [10,43,44] via IPG A-type, places these putative second messengers or mediators at the heart of metabolic regulation in the cyclic processes of protein phosphorylation/dephosphorylation, constant cycling being of prime importance as a background to rapid hormone response [45].

The present observations that there is a strong negative correlation between the concentration IPG P-type in urine and systolic blood pressure, and a significant, but less marked, positive correlation with IPG A-type (FIGS. 6A,B), deserve more detailed consideration in the light of the importance of hypertension as a factor in syndrome X [5,6], and the fact that approximately 40% of individuals with NIDDM are hypertensive and have an increased risk of cardiovascular disease [46].

The question arises as to the manner in which the IPGs might link, directly or indirectly, with systems influencing blood pressure. Derangements in NIDDM in two major systems linked to regulation of blood pressure have been reviewed recently, these are the role of the sympathoadrenal system [42], and the potential role of the endothelium-derived nitric oxide system (EDNO) [47]. An involvement of IPG P-type in the generation of NO by endothelial cells would be a particularly attractive hypothesis.

Baron [47] has provided evidence for the linking the EDNO system in insulin action which rests on the observations that:

(a) Insulin produces a specific increase in blood flow in skeletal muscle.

(b) Insulin stimulation of glucose uptake by muscle is associated with increased vasodilation.

(c) That insulin mediated vasodilation occurs by the release of NO as indicated by the use of inhibitors of NO synthase activity.

(d) The effect of insulin on the dose response curve for methacholine (an acetylcholine-type compound which cause the synthesis and release of EDNO), is shifted to the left, consistent with insulin modulation the synthesis/release of EDNO. Evidence suggesting that insulin causes an increase in the production of EDNO in insulin sensitive individuals, but not in insulin resistant subjects, led to the proposal that the endothelium is an insulin target tissue [47].

(e) Thus, insulin resistance in obesity may be at the level of the release of NO by endothelial cells, leading to impaired vasodilation the presence of insulin. Such an impairment would, in turn, result in an associated reduction in the rate of insulin-mediated glucose uptake, and to enhanced pressor sensitivity [47]. Such an hypothesis would link the major aspects of syndrome X to the ubiquitous nitric oxide signalling system [48].

The question of the role played by IPG P-type in the sequence postulated by Baron [47] remains open to question, although the role of IPG P-type as a putative insulin second messenger, together with the present data, strongly suggests that IPGs are part of this integrated system. The association of manganese with IPG P-type, is of interest in this context, not only for the requirement for manganese by the guanylate cyclase system, associated with the generation of cGMP in the smooth muscle relaxant signal initiated by NO, but also for the adducts formed between manganese and NO [49], suggesting a possible role for IPG P-type in the transport and/or sequestering of this cellular signalling molecule, with, perhaps, special reference to the regulation of protein phosphatase-1 [50].

The present data, taken in conjunction with new concepts un the importance of endothelial cell function in pathophysiological states, focuses attention on the possible significance of IPGs as central factors in the aetiology of syndrome X.

3. Aspects of the Use of Insulin and IPGs in Treatment of NIDDM:

The treatment of diabetic patients is a subject continuously under review, perhaps most marked for those with NIDDM; a number of prospective studies have been undertaken to assess the best regime [see 38]. With respect to treatment by injection of insulin, criticisms include the fact that this means of administration results in high peripheral insulin levels, possibly contributing to abnormalities in lipid metabolism and vascular complications, the physiological route of release into the portal circulation and delivery to the liver being by-passed [51]. Recent studies by Kubot et al [52] have provided evidence demonstrating the superiority of portal insulin delivery on portally loaded glucose handling over peripheral deliver, a matter which has been the subject of some controversy [see 52]. The oral administration of IPGs would have the potential advantage of portal delivery, thus approaching a more normal physiological relationship between the putative mediators of insulin action and the disposal of an ingested glucose load.

Secondly, when relatively high levels of insulin are administered to achieve an acceptable level of blood glucose control, as in severe insulin resistance, there is the danger of inappropriate stimulation of tissues by cross-reactivity of insulin with IGF-I receptors [53]. The appearance of skin lesions of acanthosis nigricans and ovarian cell thecal hyperplasia with hyperandrogenism are reported to be associated with insulin resistance; theca cells possess both insulin and IGF-I receptors which can signal increased steroidogenesis [53]. O'Rahilly & Moller reported that although insulin receptor mutations are uncommon in patients with typical NIDDM, there is a practical problem of treating individuals with severe insulin resistance associated with such mutations, and they cite the use of IGF-I as a treatment for some cases.

For several decades a family of drugs, the sulphonylureas, has been a major therapeutic agent in the treatment of NIDDM; and, indeed, in the USA when the biguanide, phenformin, was withdrawn from the market [54], sulphonylureas were the only type of compound available for the treatment of NIDDM, although recently the biguanide metformin was approved by the Food and Drug Administration for use in the USA [55]. The metabolic disturbances of NIDDM are widely held to be the resultant effect of an interaction between insulin resistance and impaired insulin secretion [55,56]. There is evidence that the sulphonylureas act both in causing an acute stimulation of the rate of insulin release from the pancreas, and in increasing glucose uptake and utilization by extrapancreatic tissues, with evidence for sulphonylureas enhancing basal and insulin-stimulated glucose transport and metabolism in muscle and adipose tissue in animals and in humans (see Muller et al [57]). The observation that a sulphonylurea drug, glimpiride, stimulates the release of glycosyphosphatidlyinositol-anchored plasma-membrane proteins from 3T3 adipocytes was of particular interest in the present context, since this potent insulin-mimetic drug appeared to have common features with the putative insulin second messenger system of the inositol phosphoglycans [9–15 12,58]. It is important to note, however, that glimpirides have not been shown to induce the cleavage of free GPIs, the IPG precursors.

This evidence for a possible common locus of action between insulin and a sulphonylurea in releasing a precursor of inositol phosphoglycan from cell membranes reinforces, in some measure, the view that inositol phosphoglycans have a potential for therapeutic use in the treatment of NIDDM. The importance of the present invention in suggesting treatment of diabetes with IPGs per se, as an alternative to using a drug liberating IPG precursors, is perhaps indicated by the statement in A recent review that "Patients with overt NIDDM have reduced responses to many insulin secretagogues, including glucose and non-glucose stimuli, such as sulphonyulureas, arginine, and leucine. Patients treated with sulphonylureas have high primary and secondary failure rates." [56]. Thus, based on the study here, inositol phosphoglycans, and/or their precursors, might be more effective in patients failing to respond fully to treatment with sulphonylureas by normalisation of blood glucose.

The biguanide, metformin is the treatment widely chosen for treatment of diabetic patients with NIDM, insulin resistance and obesity [37]. While this drug reduces fasting glucose levels and reduces hepatic glucose production [37, 55], it clearly fails to restore the pattern of excretion of IPG P-type to normal, this marker remaining significantly below control values in the present survey (FIGS. 5A,B). The apparent failure of metformin to restore the IPG P-type to normal values may have a bearing on the lactic acidosis found with this class of compound, seen most notably with the biguanide, phenformin, now withdrawn. While lactic acidosis is a relatively minor problem when metformin is given to selected patients free from hepatic or renal disease, it remains a factor to be considered as a potential hazard in some individuals [37,55]. On the basis of the present work, it is suggested that an inappropriately low IPG P-type might be associated with a diminished activity of PDH phosphatase and an associated alteration in the active inactive forms of PDH, leading to the diversion of pyruvate generated in the glycolytic pathway to lactic acid.

On the basis of current problems with conventional treatments, some of which are outlined, there would appear to be a case for considering the use of IPGs or of precursors or of antagonists of the compounds, as an adjunct in the treatment of diabetes. Among the positive aspects of the use of IPGs are the small molecular weight and heat and acid stability; thus, these compounds should be suitable for oral administration, and delivery to the live, via the hepatic portal circulation, might avoid some of the problems associated with peripheral tissue overload with insulin [51,52].

It is probable that a fine balance exists between IPG P-type and IPG A-type, which preliminary data suggests may be tissue specific in response to hormone stimuli [13]. The knowledge of the structure and function of these second messengers offers a new avenue to the understanding and treatment of diabetes.

TABLE 1

Some Properties of Inositol Phosphoglycans

| | IPG P-Type | IPG A-Type |
|---|---|---|
| CHEMICAL COMPONENTS | | |
| | Cyclitol | Cyclitol |
| | Carbohydrates | Carbohydrates |
| | Phosphate | Phosphate |
| | Metal ($Mn^{2+}/Zn^{2+}$) | Metal ($Zn^{2+}$) |
| SEPARATION | | |
| AG 1-x8 | pH 2.0 | pH 1.3 |
| BIOACTIVITY | | |
| Activation of: | Pyruvate DH P'ase | Lipogenesis |
| | Glycogen synthase | Acetyl CoA carbox. |
| | | Low-km cAMP |
| | | phosphodiesterase |
| Inhibition of: | cAMP - PK | cAMP - PK |
| | G6P phosphatase | Adenylate cyclase |
| METABOLIC EFFECTS | | |
| | Increased glucose utilisation by muscle via oxidation (PDH) & glycogen synthesis (70% of glucose load used by muscle) | Increased lipid Lowers cAMP - counteracting effect of catecholamines e.g. on lipolysis |

↓

Jointly promote dephosphorylation of enzymes regulated by phosphorylation-dephosphorylation cycle

TABLE 2

Reported changes in free Chiro- and Myo-Inositol in urine of NIDDM subjects (estimated by GC/MS of derivatised product)

Chiro-inositol
Decreased in urine of
NIDDM subjects

| Normal 89: | NIDDM 1.8 umol/day [22] |
| Normal 96: | NIDDM 32 umol/day [23] |

Increased in urine of
NIDDM subjects

| Normal 2.1: | NIDDM 12 umol/day [26] |

Myo-inositol
Increased in urine of
NIDDM subjects

| Normal 176: | NIDDM 444 umol/day [22] |
| Normal 86: | NIDDM 825 umol/day [26] |

Reported changes in mediator activity of IPG P-Types and IPG A-Types in urine of NIDDM subjects
(estimated by bioassay - PDH P'ase, cAMP PK)
IPG P-Type (chiro-inositol containing)
Decreased in urine of NIDDM subjects [25]
IPG A-Type (myo-inositol containing)
Unchanged in urine of NIDDM subjects [25]
(Note: only 9 controls and 4 NIDDM subjects, assays non-linear)

[22] Kennington et al. 1990; [23] Suzuki et al. 1994; [25] Asplin et al. 1993; [26] Ostlund et al. 1993

TABLE 3a

The IPG A-type and IPG P-type content of urine from normal and diabetic (IDDM and NIDDM) male subjects.

| GROUP | IPG A-TYPE | IPG P-TYPE | IPG-P / IPG-A | IPG A-type | IPG P-type | CREATININE |
|---|---|---|---|---|---|---|
| | (% stimulation by 10 ml urine) | | | (Units/mmol creatinine) | | (mmol/L) |

URINARY IPG A-TYPE AND IPG P-TYPE IN GROUPS OF DIABETIC AND CONTROL MALE SUBJECTS

VALUES EXPRESSED AS MEANS ± SEM

| | | | | | | |
|---|---|---|---|---|---|---|
| CONTROLS (27) | 29.2 ± 3.7 | 89.3 ± 8.3 | 3.06 | 7.86 ± 1.56 | 21.6 ± 2.54 | 9.86 ± 0.93 |
| DIABETICS (30) | 67.5 ± 11.1 | 98.6 ± 12.1 | 1.46 | 24.7 ± 4.8 | 31.1 ± 4.5 | 7.37 ± 0.56 |
| Fisher's P | <0.01 | NS | | <0.01 | NS | <0.05 |

VALUES EXPRESSED AS MEDIANS AND RANGE

| | | | | | | |
|---|---|---|---|---|---|---|
| CONTROLS (27) | 25 (71–5) | 82 (172–7) | 4.2 (15.8–0.2) | 4.88 (33.2–1.0) | 16.8 (62.1–8.3) | 8.5 (20.8–3.2) |
| DIABETICS (30) | 48 (265–2) | 81 (308–30) | 1.3 (18–0.2) | 13.5 (107–3.1) | 25.2 (139–6.6) | 6.6 (11.75–2.8) |
| Mann-Whitney test | | NS | | <0.001 | NS | <0.05 |

URINARY IPG A-TYPE AND IPG P-TYPE IN A GROUP OF NON-DIABETIC FEMALE SUBJECTS

VALUES EXPRESSED AS MEANS ± SEM

| | | | | | | |
|---|---|---|---|---|---|---|
| CONTROL FEMALE (10) | 997.8 ± 11.8 | 68.2 ± 12.3 | 0.70 | 32.7 ± 6.02 | 18.8 ± 1.96 | 7.11 ± 0.81 |
| Fisher's P (males v females) | <0.001 | NS | | <0.001 | NS | <0.05 |

TABLE 3b

Biodata - Control and Diabetic Subjects

| | CONTROLS (Non diabetic) | DIABETICS (IDDM & NIDDM) |
|---|---|---|
| No. of subjects | 27 | 30 |
| Age (years) | 51.5 ± 14.6 (29–69) | 59.7 ± 12.2 (28–82) |
| Body mass index | 24.7 ± 2.4 (22.3–30.8) | 28.0 ± 3.9 (21.9–38.5) |
| Creatinine (mmol/L) | 9.85 ± 4.6 (3.24–20.8) | 7.19 ± 3.0 (2.84–15.6) |
| HbA1 | Not measured (Normal range 5–8) | 10.8 ± 1.6 (8.5–14.7) |
| BP systolic | Not measured | 139 ± 15 (111–172) |
| BP diastolic | Not measured | 80 ± 9 (57–97) |
| Ethnic origin Caucasian/Asian | 25/2 | 19/11 |
| Treatment | | |
| Insulin alone | — | 6 |
| Insulin ± another | — | 3 |
| Metformin ± another | — | 11 |
| Sulphonylurea ± another | — | 10 |

Values are given as means ± SD with the range shown in parentheses.

TABLE 4

Insulin Resistance and Obesity.

"The mechanisms linking obesity and insulin resistance are not known"
[Walker. Obesity, insulin resistance and its link to NIDDM. 1995]

At least 30% of NIDDM patients are obese (body mass index BMI > 30) and are at increased risk or cardiovascular disease. The cluster of risk factors "syndrome X"
Insulin resistance
Glucose intolerance
High circulating insulin
Disordered lipid metabolism
Hypertension

[Reavan. Role of insulin resistance in human disease. 1988; Walker, 1995]

TABLE 5

A CHARACTERISTICS OF OBESE NIDDM SUBJECTS AND CHANGES IN IPG P- AND A-TYPES

| | | |
|---|---|---|
| OBESITY | Low P | High A |
| RAISED HbA1 (Obesity + raised HbA1 indicates glucose intolerance) | Low P | High A |
| HIGH BLOOD PRESSURE | Low P | High A |

B EFFECT OF LOW IPG P-TYPE ON METABOLIC PATHWAYS

| | | |
|---|---|---|
| GLUCOSE GLYCOGEN | Decreased | |
| PYRUVATE OXIDATION | Decreased | Glucose intolerance |
| HEPATIC GLUCOSE PRODUCTION | Increased | |

C EFFECT OF HIGH IPG A-TYPE ON METABOLIC PATHWAYS

| | | |
|---|---|---|
| LIPOGENESIS | Increased | |
| ACETYL CoA CARBOX. | Increased | Increased fat synthesis and storage |
| RAISED cAMP | Decreased | |
| LIPOLYSIS | Decreased | |

References:

1. Bennett, P. H., Bogardus, C., Tuomilehto, L. and Zimmet, P. 1992. Epidemiology and natural history of NIDDM: Non-obese and obese. In: International Textbook of Diabetes mellitus. Eds. Alberti, K. G. M. M., DeFronzo, R. A., Keen, H. and Zimmet, P. pp147–169. John Wiley & Sons Ltd.

2. Himsworth, H. P. 1936. Diabetes mellitus: its differentiation into insulin-sensitive and insulin insensitive types. Lancet i. 127–130.

3. DeFronzo, R. A. 1988. The Triumvirate: beta cell, muscle, liver: a collusion responsible for NIDDM. Diabetes, 37: 667–687.

4. DeFronzo, R. A., Bonadonna, R. C. and Ferrannini, E. 1992. Pathogensis of NIDDM. A balanced overview. Diabetes Care, 15: 318–368.

5. Reaven, G. M. 1988. Banting Lecture. Role of insulin resistance in human disease. Diabetes, 37: 1595–1607.

6. Reaven, G. M. 1995. Pathophysiology of insulin resistance in human disease. Physiol. Rev. 75: 473–486.

7. Walker, M. 1995. Obesity, insulin resistance, and its link to non-insulin-dependent diabetes mellitus. Metabolism, 44 (Suppl. 3): 18–20. p b 8. Williams, B. 1994. Insulin resistance: the shape of things to come. Lancet, 344: 521–524.

9. Larner, J., Huang, L. C., Tang, G., Susuki, S., Schwartz, C. F. M., Romero, G., Roulidis, Z., Zeller, K., Shen, T. W., Oswald, A. S., and Lutterell, L. 1998. Insulin Mediators: Structure and Formation. Cold Springs Harbor Symp. 53: 965–971.

10. Romero, G., and Larner, J., 1993. Insulin Mediators and the Mechanism of Insulin Action. Adv. Pharm. 24: 21–50.

11. Romero, G., 1991. Inositol glycans and cellular signalling. Cell Biology International reports. 15:827–852.

12. Rademacher, T. W., Caro. H., Kunjara. S., Wang, D. Y., Greenbaum, A. L. and McLean, P. 1994. Inositolphosphoglycan second messengers. Brazilian J. Med. Biol. 27:327–341.

13. Kunjara, S., Caro, H. N., McLean, P. and Rademacher, T. W. 1995. Tissue specific release of inositol phosphoglycans. In Svasti, J. et al (Eds). Biopolymers and bioproducts: Structure, function and applications. Bangkok, Thailand. Samakkhisan (Dokya). Public Co. Ltd. 301–306.

14. Romero, G., Gamez, G., Huang, L. C., Lilley, K., and Lutterell, L. 1990. Antiinositolglycan antibodies selectively block some of the actions of insulin in intact BC3H1 cells. Proc. Natl. Acad. Sci. USA. 87: 1476–1480.

15. Varese, R. V., Standaert, M. C., Yamada, K., Huang, C., Zhang, C., Cooper, D. R., Wang, Z., Yang, Y., Susuki, S., Toyota, T. and Larner, J. 1994. Insulin-induced activation of glycerol 3-phosphate acyltransferase by chiro-inositol-containing insulin mediator is defective in adipocytes of insulin resistant, type II diabetic Goto-Kakizaki rats. Proc. Natl. Acad. Sci. 91: 11040–11044.

16. Lazar, D. F., Knez, J. J., Medoff, M. E., Cuatracasa, P., and Saltiel, A. P. 1994. Stimulation of glycogen synthesis by insulin in human erythroleukemia cells requires the synthesis of glycosyl-phosphatidylinositol Proc. Natl. Acad. Sci. USA. 91:9665–9669.

17. Misek, D. E., and Saltiel, A. R. 1994. An inositol phosphate glycan derived from a Trypanosoma brucei glycosyl phosphatidylinositol promotes protein dephosphorylation in rat epidiymal adipocytes. Endocrinology, 135: 1869–1876.

18. Sanchez-Arias, J. A., Sanchez-Gutierrez, J. C., Guadano, A., Alvarez, J. F., Samper, B., Mato, J. M. and Feliu, J. E. 1992. Impairment of glycosyl-phosphatidylinositol-dependent insulin signaling system in isolated rat hepatocytes by streptozotocin-induced diabetes. Endocrinology, 131:1727–1733.

19. Villar-Palasi, C., and Farese, R. V. 1994. Impaired skeletal muscle glycogen synthase activation by insulin in the Goto-Kakizaki (G/K) rat. Diabetologia, 37: 885–888.

20. Ortmeyer, H. K., Huang, L. C., Zhang, L., Hansen, B. C., and Larner, J. 1993. Chiro-inositol deficiency and insulin resistance. II. Acute effects of D-chiro-inositol administration in streptozotocin-diabetic rats given a gloucose load, and spontaneously insulin resistance Rhesus monkeys. Endocrinology, 132: 646–651.

21. Huang, L. C., Fonteles, M. C., Houston, D. B., Hang, C., and Larner, J. 1993. Chiro-inositol deficiency and insulin resistance. III Acute glycogenic and hypoglycaemic effects of two inositol phosphoglycan insulin mediators in normal and streptozotocin-diabetic rats in vivo. Endocrinology, 132: 652–657.

22. Kennington, A. S., Hill, C. H., Craig, J., Bogardus, C., Raz, I., Ortmeyer, H. K., Hansen, B. C., Romero, G., and Larner, J. 1990. Low urinary chiro-inositol excretion in non-insulin dependent diabetes mellitus. New Engl. J. Med. 323: 373–378.

23. Suzuki, S., Tanada, Y., Hirai, S., Abe, S., Sosaki, A., Suzuki, K., Toyata, T. 1991. In: New Directions in Research and Clinical Works for Obesity and Diabetes mellitus. Eds. Angei, A., Hotta, N. pp 197–203. Elsevier.

24. Ortmeyer, H. K., Bodkin, N. L., Lilley, K, Larner, J. and Hanson, B. C. 1993. Chiro-inositol deficiency and insulin resistance in spontaneously diabetic Rhesus monkeys. Endocrinology, 132, 640–645.

25. Asplin, I., Galasko, G., and Larner, J. 1993. chiro-Inositol deficiency and insulin resistance: A comparison of the chiro-inositol- and the myo-inositol-containing insulin mediators isolated from urine, hemodialysate, and muscle of control and type II diabetic subjects. Proc. Natl. Acad. Sci. USA. 90: 5924–5928.

26: Ostlund, R. E., McGill, J. B., Herskowitz, I., Kipnis, D. M., Santiago, J. V., and Sherman, W. R. 1993 D-chiro-inositol metabolism in diabetes mellitus. Proc. Natl. Acad. Sci. USA. 90: 9988–9992.

27. Prochazka, M., Mochizuki, H., Baier, L. J., Cohen, P. T. W., and Bogardus, C. 1995. Molecular and linkage analysis of type-1 protein phosphatase catalytic b subunit gene: lack of evidence for its major role in insulin resistance in Pima Indians. Diabetologia, 38: 461–466.

28. Lilley, K., Zhang, C. L., Villar-Palasi, C., Larner, J., and Huang, L. 1992. Insulin mediator stimulation of pyruvate dehydrogenase phosphatase, Arch. Biochem. Biophys. 296: 170–174.

29. Larner, J., Huang, L. C., Suzuki, S., Tang, E., Zhang, C., Schwartz, C. F. W., Romero, G., Luttrell, L. and Kennington, A. S. 1989. Insulin mediators and the control of pyruvate dehydrogenase complex. Annals N.Y. Acad. Sci. 573: 297–305.

30. Rodbell, M. 1964. Metabolism of isolated fat cells. J. Biol. Chem. 239: 375–380.

31. Newman, J. D., Armstrong, J., McD., and Bornstein, J. 1985. Assay of insulin mediator activity with soluble pyruvate dehydrogenase phosphatase. Endocrinology 116: 1912–1919.

32. Craig, J. W., Larner, J. and Asplin, C. M. 1994. Chiroinositol deficiency and insulin resistance. In. Molecular Biology of Diabetes. Part II. Eds. Draznin, B. and LeRoith, D., humana Press Inc. Totowa. NJ.

33. Serrano, J., Mateo, C. M. and Caro, J. F. 1992. Insulin resistance: cellular and molecular mechanisms. In: recent Advances in Endocrinology and Metabolism. Vol. 4: pp. 167–183.

34. Moller, D. E. and Flier, J. S. 1991. Insulin resistance—mechanisms, syndrome, and implications, New Engl. J. Med. 325: 938–948.

35. Krentz, A. J. and Nattrass, M. 1996. Insulin resistance: a multifaceted metabolic syndrome. Insights gained using a low-dose insulin infusion technique. Diabetic Medicine, 13: 30–39.

36. Ferrannini, E. 1995. Physiological and metabolic consequences of obesity. Metabolism, 44: (Suppl.3) 15–17.

37. DeFronzo, R. A. and Goodman, A. N. and the Multicenter Metformin Study Group 1995. Efficacy of metformin in patients with non-insulin dependent diabetes mekkitus. New Engl. J. Med. 333: 541–549.

38. United Kingdom Prospective Diabetes Study (UKPDS). 13: Relative efficacy of randomly allocated diet, sulphonylurea, insulin or metformin in patients with newly diagnosed diabetes followed for three years. 1995. B,M. J. 310: (6972): 83–88.

39. Snedecor, G. W. 1964. Statistical methods. Fifth Edition. Iowa State University Press, Ames Iowa, USA.

40. Suzuki, S., Kawasaki, H., Satoh, Y., Ohtomo, M., Hirai, M., Hirai, A., Hirai, S., Onoda, M., Matsumoto, M., Hirokio, Y., Akai, H., Craig, J., Larner, J. and Toyota, T. 1994. Urinary chiro-inositol excretion is an index marker of insulin sensitivity in Japanese Type II diabetes. Diabetes Care.

41. Sochor, M., Baquer, N. Z. and McLean, P. 1985. Glucose over-and under-utilization in diabetes. Comparative studies of changes in activities of enzymes of glucose metabolism in rat kidney and liver. Molecular Physiol. 2: 51–68.

42. Reaven, G. M., Lithel, H. and Landsberg, L. 1996. Hypertension and associated metabolic abnormralitia—the role of insulin resistance and the sympathoadrenal system. New Engl. J. Med. 334: 374–381.

43. Machicao, F., Mushack, J., Seffer, E., Ermel, B. and Haring, H. U. 1990: Mannose, glucosamine and inositol monophosphate inhibit the effects of insulin on lipogenesis. Further evidence for a role for inositol oligosaccharides in insulin action. Biochem. J. 266: 909–916.

44. Martiny, L., Antonicelli, F., Thuillez, B., Lambert, B., Jacquemin, C., and Haye, B. 1990: Control by thyotropin of the production by thyroid cells of an inositol phosphate-glycan. Cell Signalling 2: 21–27.

45. Brautigan, D. L 1994. Protein phosphatases. Recent Prog. Hormone Res. 49: 197–214.

46. Panzram, G., 1987. Mortality and survival in type (non-insulin-dependent) diabetes mellitus. Diabetologia, 30: 123–131.

47. Baron, A. D. 1996. The coupling of glucose metabolism and perfusion in human skeletal muscle. The potential role of endothelium-derived nitric oxide. Diabetes, 45 (Suppl. 1): S105–S109.

48. Moncada, S. and Higgs, A. 1993. Mechanisms of disease: the 1-arginine nitric oxide pathway. New Engl. J. Med. 329: 2002–2012.

49. Cotten, F. A. and Wilkinson, G. 1972. Advanced Inorganic Chemistry. Third edition, Interscience publishers. New York, London.

50. Cohen, P. 1989. The structure and regulation of protein phosphatases. Annu. Rev. Biochem. 58: 453–508.

51. Alberti K. G. M. M. and Press, C. M. 1982. The Biochemistry of the Complications of Diabetes Mellitus. pp 231–270. Eds Keen, H. and Jarret, J. Publishers Edware Arnold Ltd, London.

52. Kubota, M., Yamasaki, Y., Sekiya, M., Kubota, M., Morishima, T., Kishimoto, R., Shichiri, M and Kamada, T. 1996. Portal insulin delivery is superior to peripheral delivery in handling of portally delivered glucose. Metabolism, 45: 150–154.

53. O'Rahilly, S. and Moller, D. E. 1992. Mutant insulin receptors in syndromes of insulin resistance. Clinical Endocrinology, 36: 121–132.

54. Williams, R. H. and Palmer, J. P. 1975. Farewell to phenformin for treating diabetes mellitus. Ann. Intern. Med. 83: 567–568.

55. Sturnvoll, M., Nurjhan, N., Perriello, G., Dailey, G. and Gerich, J. E. 1995. Metabolic effects of metformin in non-insulin-dependent diabetes mellitus. New Engl. J. Med. 333: 550–554.

56. Polansky, K. S., Sturis, J. and Bell, G. I. 1996. Non-insulin-dependent diabetes mellitus—a genetically programmed failure of the beta cell to compensate for insulin resistance. New Engl. J. Med. 334: 777–783.

57. Muller, G., Dearey, E. A. and Punter, J. 1993. The sulphonylurea drug, glimepiride, stimulates release of glycosylphosphatidylinositol-anchored plasma-membrane proteins from 3T3 adipocytes. Biochem. J. 289: 509–521.

58. Romero. G., Lutterll, A., Rogol, A., Zeller, K., Hewlett, E. and Larner, J. 1988. Phosphatidylinositol-glycan anchors of membrane proteins; potential precursors of insulin mediators. Science (Wash. DC) 240: 509–512.

What is claimed is:

1. A method of diagnosing diabetes, the method comprising determining: (a) the level of P- or A-type inositolphosphoglycans (IPGs), (b) the ratio of P-type to A-type IPGs, or (c) the ratio of A-type to P-type IPGs in a biological sample from a patient, wherein:

an increased level of A-type IPGs, a reduced P-type to A-type IPG ratio, or an increased A-type to P-type IPG ratio, as compared to a control level or ratio, is indicative of obese type II diabetes; or an increased level of P-type IPGs, an increased P-type to A-type IPG ratio, or a reduced A-type to P-type IPG ratio, as compared to a control ratio, is indicative of lean type II diabetes; and the level of P-type IPGs is determined using an assay selected from the group consisting of measurement of activation of pyruvate dehydrogenase phosphatase and an immunoassay, and the level of A-type IPGs is determined using an assay selected from the group consisting of measurement of activation of lipogenesis in isolated adipocytes and an immunoassay.

2. The method of claim 1 wherein the biological sample is a blood or urine same.

3. The method of claim 1 wherein the level of the P- or A-type IPGs is determined using an assay measuring activation of pyruvate dehydrogenase phosphatase and/or activation of lipogenesis in isolated adipocytes, respectively.

4. The method of claim 3 wherein the level of the P-type IPGs is determined in an assay measuring activation of pyruvate dehydrogenase phosphatase by P-type IPGs.

5. The method of claim 3 wherein the level of the A-type IPGs is determined in an assay measuring activation of lipogenesis by A-type IPGs in isolated adipocytes.

6. The method of claim 1 wherein the level of the P- and/or A-type IPGs is determined using an immunoassay.

7. The method of claim 6 wherein the level of the P-type IPGs is determined using an immunoassay.

8. The method of claim 1 comprising:

(a) contacting a biological sample obtained from the patient with a solid support having immobilised thereon a first antibody having one or more binding sites specific for one or more P-type IPGs and a second antibody having one or more binding sites specific for one or more A-type IPGs;

(b) contacting the solid support with labelled developing agents capable of binding to IPGs bound to antibodies or capable of binding to anti-IPG antibodies; and, (c) detecting the label of the developing agents specifically binding in (b) to obtain values representative of the levels of the P- and A-type IPGs in the sample.

9. The method of claim 6 wherein wherein the level of the A-type IPGs is determined using an immunoassay.

10. The method of claim 6 wherein the biological sample is a blood or urine sample.

11. The method of claim 8 wherein the biological sample is a blood or urine sample.

12. The method of claim 8 wherein at least one labelled developing agent is capable of binding to bound IPGs.

13. The method of claim 1 wherein the patient is a patient suspected of having type II diabetes.

14. The method of claim 13 wherein the type II diabetes is obese type II diabetes, and:
   a P-type to A-type IPG ratio less than about 2 times the ratio in control subjects is indicative of obese type II diabetes; and
   an A-type to P-type IPG ratio greater than about 2 times the ratio in control subjects is indicative of obese type II diabetes.

15. The method of claim 1, wherein an IPG ratio is determined.

16. A method of diagnosing obese type II diabetes, the method comprising determining: (a) the level of A-type inositolphosphoglycans (IPGs), (b) the ratio of P-type to A-type IPGs, or (c) the ratio of A-type to P-type IPGs in a biological sample from a patient, wherein said P-type IPGs are capable of activating pyruvate dehydrogenase phosphatase, and said A-type IPGs are capable of activating lipogenesis in isolated adipocytes;
   wherein a level of A-type IPGs or an A-type to P-type IPG ratio that is more than about 2-fold higher, or a P-type to A-type IPG ratio that is more than about 2-fold lower, than in control subjects is indicative of obese type II diabetes; and
   wherein the IPG levels are determined by immunoassay.

17. The method of claim 16 wherein the biological sample is a blood or urine sample.

18. The method of claim 17, the method comprising:
   (a) contacting the sample with a solid support having immobilised thereon a first antibody having one or more binding sites specific for one or more P-type IPGs and a second antibody having one or more binding sites specific for one or more A-type IPGs;
   (b) contacting the solid support with labelled developing agents capable of binding to IPGs bound to antibodies or capable of binding to anti-IPG antibodies; and
   (c) detecting the label of the developing agents specifically binding in (b) to obtain values representative of the levels of the P- and A-type IPGs in the sample.

19. The method of claim 18 wherein (i) at least one of the immobilized first and second antibodies comprises a monoclonal antibody, (ii) after contact with the sample, the solid support is contacted with a polyclonal antibody capable of specifically binding to IPGs, and (iii) the developing agent comprises an antibody capable of specifically binding to the polyclonal antibody.

20. The method of claim 16 wherein the patient is a patient suspected of having type II diabetes.

21. The method of claim 11 wherein the type II diabetes is obese type II diabetes.

22. The method of claim 16, wherein an IPG ratio is determined.

23. A method of diagnosing lean type II diabetes, the method comprising determining:
   (a) the level of P-type inositolphosphoglycans (IPGs), (b) the ratio of P-type to A-type IPGs, or
   (c) the ratio of A-type to P-type IPGs in a biological sample from a patient, wherein said P-type IPGs are capable of activating pyruvate dehydrogenase phosphatase, and said A-type IPGs are capable of activating lipogenesis in isolated adipocytes;
   wherein a level of P-type IPGs or a P-type to A-type IPG ratio that is more than about 2-fold higher, or an A-type to P-type IPG ratio that is more than about 2-fold lower, than in control subjects is indicative of lean type II diabetes;
   wherein the IPG levels are determined by immunoassay.

24. The method of claim 23 wherein the biological sample is a blood or urine sample.

25. The method of claim 24, the method comprising:
   (a) contacting the sample with a solid support having immobilised thereon a first antibody having one or more binding sites specific for one or more P-type IPGs and a second antibody having one or more binding sites specific for one or more A-type IPGs;
   (b) contacting the solid support with labelled developing agents capable of binding to IPGs bound to antibodies or capable of binding to anti-IPG antibodies; and
   (c) detecting the label of the developing agents specifically binding in (b) to obtain values representative of the levels of the P- and A-type IPGs in the sample.

26. The method of claim 25 wherein (i) at least one of the immobilized first and second antibodies comprises a monoclonal antibody, (ii) after contact with the sample, the solid support is contacted with a polyclonal antibody capable of specifically binding to IPGs, and (iii) the developing agent comprises an antibody capable of specifically binding to the polyclonal antibody.

27. The method of claim 23 wherein the patient is a patient suspected of having type II diabetes.

28. The method of claim 27 wherein the type II diabetes is lean type II diabetes.

29. The method of claim 23, wherein an IPG ratio is determined.

* * * * *